(12) United States Patent
Chibber et al.

(10) Patent No.: US 8,609,633 B2
(45) Date of Patent: *Dec. 17, 2013

(54) CORE 2 GLCNAC-T INHIBITORS

(75) Inventors: Rakesh Chibber, Exeter (GB); Russell Hagan, London (GB)

(73) Assignee: MS Therapeutics Limited (GB)

( * ) Notice: Subject to any disclaimer, the term of this patent is extended or adjusted under 35 U.S.C. 154(b) by 0 days.

This patent is subject to a terminal disclaimer.

(21) Appl. No.: 13/331,250

(22) Filed: Dec. 20, 2011

(65) Prior Publication Data

US 2012/0142620 A1 Jun. 7, 2012

Related U.S. Application Data

(63) Continuation of application No. 11/481,255, filed on Jul. 6, 2006, now abandoned.

(30) Foreign Application Priority Data

Jul. 6, 2005 (GB) .................................. 0513888.8

(51) Int. Cl.
*A01N 43/04* (2006.01)
*A61K 31/715* (2006.01)

(52) U.S. Cl.
USPC ............................................. 514/61; 514/54

(58) Field of Classification Search
None
See application file for complete search history.

(56) References Cited

U.S. PATENT DOCUMENTS

| | | | |
|---|---|---|---|
| 4,602,003 A | 7/1986 | Malinow |
| 5,104,856 A | 4/1992 | Esko et al. |
| 5,360,733 A | 11/1994 | Fukuda et al. |
| 5,461,143 A | 10/1995 | Wong et al. |
| 5,470,879 A | 11/1995 | Sauvaire et al. |
| 5,486,510 A | 1/1996 | Bouic et al. |
| 5,589,182 A | 12/1996 | Tashiro et al. |
| 5,624,832 A | 4/1997 | Fukuda et al. |
| 5,658,778 A | 8/1997 | Fukuda et al. |
| 5,684,134 A | 11/1997 | Fukuda et al. |
| 5,827,884 A | 10/1998 | Obagi |
| 5,843,707 A | 12/1998 | Larsen et al. |
| 5,880,091 A | 3/1999 | Cummings et al. |
| 5,886,029 A | 3/1999 | Dhaliwal |
| 5,952,393 A | 9/1999 | Sorkin, Jr. |
| 5,958,770 A | 9/1999 | Cham et al. |
| 5,965,449 A | 10/1999 | Novak |
| 5,985,936 A | 11/1999 | Novak |
| 5,997,877 A | 12/1999 | Chang |
| 6,042,834 A | 3/2000 | Baraka |
| 6,087,353 A | 7/2000 | Stewart et al. |
| 6,131,578 A | 10/2000 | King et al. |
| 6,197,832 B1 | 3/2001 | Sorkin, Jr. |
| 6,294,157 B1 | 9/2001 | Rubinstenn et al. |
| 6,346,267 B1 | 2/2002 | Fry et al. |
| 6,383,514 B1 | 5/2002 | Weitkemper et al. |
| 6,407,085 B1 | 6/2002 | Kief |
| 6,451,355 B1 | 9/2002 | Reisner |
| 6,593,301 B1 | 7/2003 | Ma et al. |
| 6,635,461 B1 | 10/2003 | Schwientek et al. |
| 6,787,151 B2 | 9/2004 | Meijer et al. |
| 6,933,291 B2 | 8/2005 | Qi et al. |
| 6,998,501 B1 | 2/2006 | Wright et al. |
| 2002/0016314 A1 | 2/2002 | Schersl |
| 2002/0018811 A1 | 2/2002 | Penteado et al. |
| 2002/0098563 A1 | 7/2002 | Korczak et al. |
| 2002/0107292 A1 | 8/2002 | Bortlik et al. |
| 2002/0156051 A1 | 10/2002 | Kutney et al. |
| 2002/0183294 A1 | 12/2002 | Barraclough et al. |
| 2002/0193317 A1 | 12/2002 | Xia et al. |
| 2003/0004147 A1 | 1/2003 | Barraclough et al. |
| 2003/0096316 A1 | 5/2003 | Wester |
| 2003/0148962 A1 | 8/2003 | Guan et al. |
| 2004/0033521 A1 | 2/2004 | Korczak et al. |
| 2004/0038923 A1 | 2/2004 | Marth et al. |
| 2004/0049352 A1 | 3/2004 | Andre et al. |

(Continued)

FOREIGN PATENT DOCUMENTS

CA 2 186987 4/1998
CA 2 335 436 8/2001

(Continued)

OTHER PUBLICATIONS

Zheng et al. Steroids (2004), vol. 69, pp. 111-119.*
Hu et al. Planta Medica (1997), vol. 63, pp. 161-165.*
Matsuda et al, Bioorg. Med. Chem. Left., vol. 13, pp. 1101-1106 (2003).
Gabor M. Models of acute inflammation in the Ear. From: *Methods in Molecular Biology*, vol. 225: Inflammation Protocols Edited by: P. G. Winyard and D. A. Willoughby © Humana Press Inc., Totowa, NJ: p. 129-137. (2003).
Sauvaire Y. et al Implication of steroidal saponins and sapogenins in the hypocholesterolaemic effect of fenugreek. Lipds 26, 191-197 (1991).

(Continued)

*Primary Examiner* — Patrick Lewis
(74) *Attorney, Agent, or Firm* — Brown Rudnick LLP

(57) ABSTRACT

A method of treating a subject in need of therapy for a condition involving detrimental activity of the enzyme core 2 GlcNAc-T is provided, comprising administration of a therapeutically effective amount of an inhibitor of core 2 GlcNAc-T of formula I to a patient in need thereof

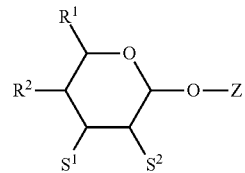

wherein:
$R^1$ is H, $C_{1-6}$ alkyl, $C_{1-6}$ hydroxyalkyl, $C_{1-6}$ alkoxy or $C_{1-6}$-alkoxy-$C_{1-6}$-alkyl;
$R^2$ is H, —OH or $C_{1-6}$ alkoxy;
$S^1$ and $S^2$ are independently selected saccharide moieties; and
Z is a steroid moiety;
or a pharmaceutically acceptable salt, ether or ester thereof.

25 Claims, 2 Drawing Sheets

(56) References Cited

U.S. PATENT DOCUMENTS

Figure 1:
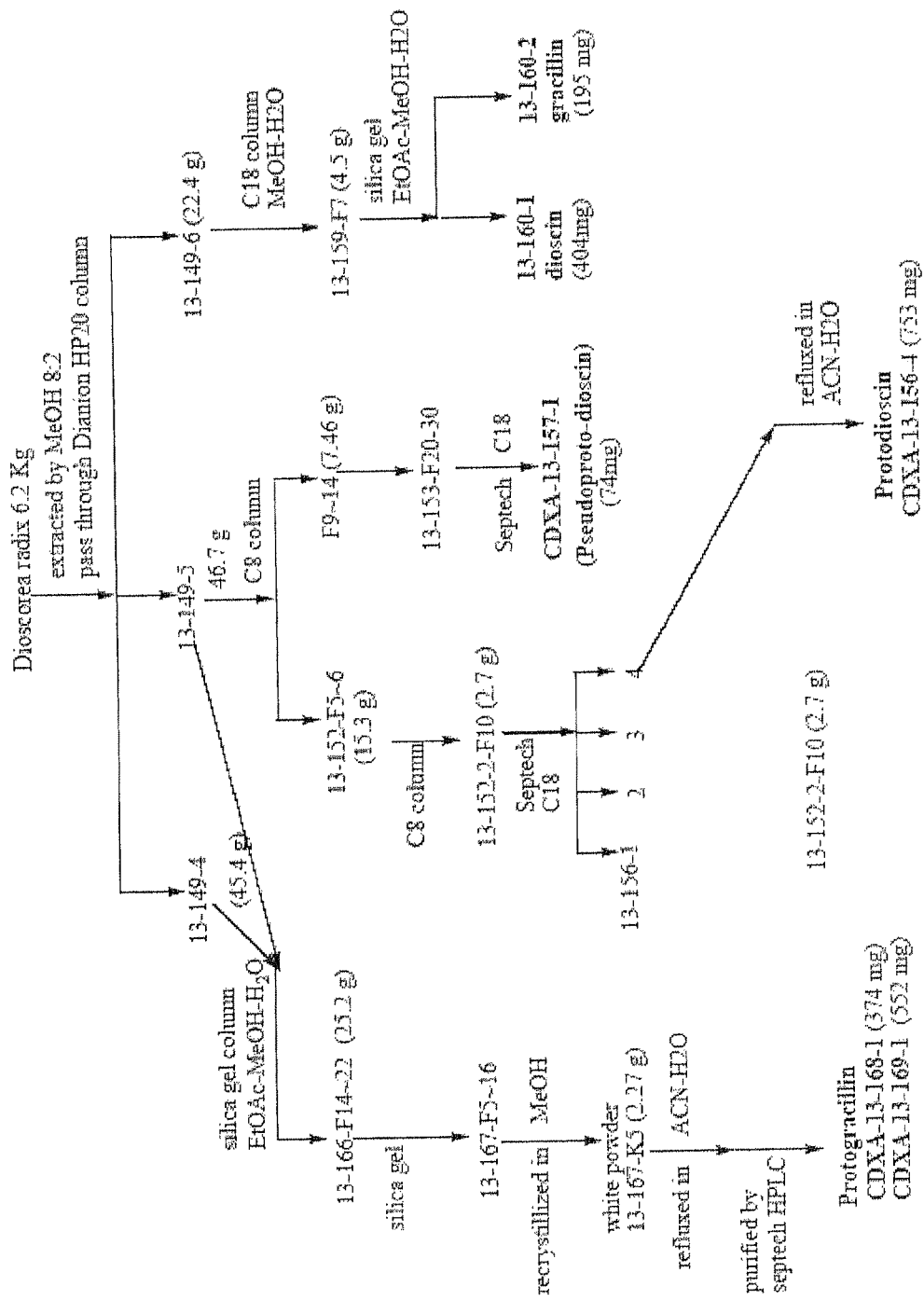

| | | |
|---|---|---|
| 2004/0203111 A1 | 10/2004 | Schwientek et al. |
| 2004/0220115 A1 | 11/2004 | Cham |
| 2004/0249138 A1 | 12/2004 | Lawson |
| 2006/0052351 A1 | 3/2006 | Platt et al. |
| 2007/0254847 A1 | 11/2007 | Liu et al. |
| 2008/0318875 A1 | 12/2008 | Chibber |

FOREIGN PATENT DOCUMENTS

| | | |
|---|---|---|
| CN | 1 237 583 A | 12/1999 |
| CN | 1237583 A | 12/1999 |
| CN | 1243129 A | 2/2000 |
| CN | 1361111 A | 12/2000 |
| CN | 1361111 A | 7/2002 |
| CN | 1 397 545 | 2/2003 |
| CN | 1 511 535 | 7/2004 |
| CN | 1 562 064 A | 1/2005 |
| DE | 4303214 A1 | 11/1994 |
| EP | 0 251 197 A2 | 1/1988 |
| EP | 0 251 197 A3 | 1/1988 |
| EP | 1 316 608 A1 | 6/2003 |
| EP | 0 850 243 B1 | 10/2003 |
| EP | 1 800 685 A1 | 6/2007 |
| JP | 03271224 A | 3/1991 |
| JP | 2004-143126 | 5/2004 |
| RU | 2 027 434 C1 | 1/1995 |
| RU | 2027434 | 1/1995 |
| SU | 833254 | 5/1981 |
| WO | WO 95/17182 A1 | 6/1995 |
| WO | WO 95/21199 A1 | 8/1995 |
| WO | WO 95/35294 A1 | 12/1995 |
| WO | WO 97/06176 A2 | 2/1997 |
| WO | WO 97/47298 A1 | 12/1997 |
| WO | WO 98/06405 A1 | 2/1998 |
| WO | 98/14459 | 4/1998 |
| WO | WO 98/33494 | 8/1998 |
| WO | WO 98/33494 A1 | 8/1998 |
| WO | WO 99/25197 | 5/1999 |
| WO | WO 99/25197 A1 | 5/1999 |
| WO | WO 99/39715 A1 | 8/1999 |
| WO | WO 99/53925 A1 | 10/1999 |
| WO | WO 00/31109 | 6/2000 |
| WO | WO 00/31109 A1 | 6/2000 |
| WO | WO 00/52029 A1 | 9/2000 |
| WO | WO 00/61153 | 10/2000 |
| WO | WO 00/78789 A1 | 12/2000 |
| WO | WO 01/32679 A2 | 5/2001 |
| WO | 01/58932 | 8/2001 |
| WO | WO 01/83717 A2 | 11/2001 |
| WO | WO 02/03996 A1 | 1/2002 |
| WO | WO 02/24212 A1 | 3/2002 |
| WO | WO 02/069980 A2 | 9/2002 |
| WO | WO 02/87548 | 11/2002 |
| WO | WO 02/087548 A1 | 11/2002 |
| WO | 03/043433 | 5/2003 |
| WO | 03/066679 | 8/2003 |
| WO | WO 03/070261 A1 | 8/2003 |
| WO | WO 03/075931 A1 | 9/2003 |
| WO | 03/092394 | 11/2003 |
| WO | WO 2004/002497 A1 | 1/2004 |
| WO | WO 2004/019960 A2 | 3/2004 |
| WO | WO 2004/029068 A1 | 4/2004 |
| WO | WO 2004/048938 A2 | 6/2004 |
| WO | WO 2004/062675 A1 | 7/2004 |
| WO | WO 2004/064852 A1 | 8/2004 |
| WO | 2004/074461 | 9/2004 |
| WO | WO 2004/093662 A2 | 11/2004 |
| WO | WO 2004/111196 A2 | 12/2004 |
| WO | WO 2005/060977 A1 | 7/2005 |
| WO | WO 2005/084323 A2 | 9/2005 |
| WO | WO 2005/120535 A1 | 12/2005 |
| WO | 2006/034655 | 4/2006 |
| WO | WO 2006/034655 A1 | 4/2006 |
| WO | WO 2006/034655 A1 | 6/2006 |

OTHER PUBLICATIONS

M. Al-Habori and Am Ala Raman Pharmacological properties, in Fenugreek the genus Trigonella Edited by Georgios a. Petropoulos; Published by Taylor & Francis Inc, New York. pp. 162-182 (2002).
N. M. Ammar, et al "Study of the Anti-Inflammatory Activity of Some Medicinal Edible Plants Growing in Egypt" Journal of Islamic Academy of Sciences 10:4, 113- 122, (1997).
H. Skalsta, Chemical Constituents, in Fenugreek, The genus *Trigonella* Edited by Georgios A. Petropoulos; Published by Taylor & Francis Inc, New York. pp. 162-182 (2002).
Guo et al Microwave assisited extraction of effective constituents of a Chinese herbal medicine *Radix puerariae*. Analytica Chimica Acta, vol. 436, p. 41-47, (2001).
Akhov L.S. et al, Biological activity of Deltoside from *Alium nutans*. In: W. Oleszek and A. Marston (eds.), Saponins in Food, Feedstuffs and Medicinal Plants, Klewer Academic Publishers. p. 22'7-23, (2000).
Deepak M., Quantitative determination of the major saponins mixture, Bacopaside A, in *Bacopa monnieri* by HPLC. Phytochemical analysis, 16 p. 24-29 (2005).
Garai S., Bacopasaponin D, a pseudojujubogenin glycoside from *Bacopa monnieri*. Phytochemistry 43, No. 2, p. 447-449. (1996).
Hosney M., Balanitoside, a furostanol glycoside and 6-methyl diosgenin, from *Balanites aegyptiaca*. Phytochemistry vol. 31, No. 10, p. 3565-3569, (1992).
K. Hostettman and A. Marston., Chemistry and Pharmacology of Natural Products—Saponins Published by Cambridge University Press. Extract pages (1995). Extract.
Kim et al., Chemical synthesis of 15-ketosterols and their inhibition of Cholesteroyl ester transfer protein. Bioorganic and medicinal chemistry, vol. 3 No. 4, p. 367-374. (1995).
Mimaki Y. et al ., Steroidal saponins from the bulbs of *Lilium brownii*; Phytochemistry, vol. 29, No. 7, p.2267-2271, (1990).
K. Maemura and M. Fukuda, "Poly-N-acetyllactosaminyl O-Glycans Attached Leukosialin—The Presence of Sialyl Lex Structures in O-Glycans" J. Biol. Chem., 267:34, pp. 24379-24386. (1992).
Mori K. et al ., Synthesis of some analogues of Blattellastanoside A, the steroidal aggregation pheromone of the German cockroach. Bioorgainic and medicinal chemistry, vol. 4 No. 3, p. 401-408, (1996).
On K. et al., Norlanostane and Lanostane glycosidesfrom the bulbs of *Chionodoxa luciliae* and their cytotoxic activity. Chem. Pharm. Bull. vol. 51(2) 92-95 (2003).
Takahashi T.. et al., Increased spontaneous adherence of neutrophils from type 2 diabetic patients with overt proteinuria. Diabetes care, vol. 23 No. 3, p. 417-418, (2000).
Vasileva et al., Steroid glycosides from suspension cultures of *Dioscorea deltodea* cells and their biological activity. In: Saponins used in traditional and modern medicine. Eds Waller and Yamasaki. Plenum Press, New York. (1996).
Yamishita T., Structures of three new steroidal alkaloids: solavarines I, II and III from *Solanum toxicarium* and *S. verbascifolium*. Chem. Pharm. Bull. 38(3) p. 827-829. (1990).
Yang X. et al., The effect of TNF alpha on glycosylation pathways in bovine synoviocytes. Biochem. Cell. Biol. 82, p. 559-568. (2004).
B. Dang et al, Increased PSGL-1 expression on granulocytes from allergic asthmatic subjects results in enhanced leukocyte recruitment under flow conditions. J. Leukocyte Biol. 72, 702-710 (2002).
R. L. Dedrick et al, "Adhesion Molecules as Therapeutic Targets for Autoimmune Diseases and Transplant Rejection." Expert Opin. Biol. Ther. 3(1): 85-89 (2003).
Y. Mimaki et al, "Steroidal Saponins From the Rhizomes of *Paris polyphylla* var. *Chinensis* and Their Cytotoxic Activity on HL-60 Cells" Natural Product Letters14(5), pp. 357-364 (2000).
Purdie D., and Irine J. C., Synthesis from glucose of an octamethylated disaccharide: Methylation of sucrose and maltose. J. Chem. Soc. 87, 1022 (1905).
J.-F. Theoret, "P-Selectin Antagonism With Recombinant P-Selectin Glycoprotein Ligand-1 (rPSGL-1g) Inhibits Circulating Activated Platelet Binding to Neutrophils Induced by Damaged Arterial Surfaces" The Journal of Pharmacology and Experimental Therapeutics, 298, 658-664 (2001).

(56) References Cited

OTHER PUBLICATIONS

Higgins E. et al., Abberant O-linked oligosaccharide in lymphocytes and platelets from patients with the Wiskott Aldrich syndrome. J. Biol Chem., 266(10), p. 6280-6290 (1991).
Yang, D.-J.et al; "Simultaneous Determination of Furostanol and Spirostanol Glycosides in Taiwanese Yam (*Dioscorea spp.*) Cultivars by High Performance Liquid Chromatography"; *Journal of Food and Drug Analysis*; vol. II, No. 4, pp. 271-276 (2003).
Hoff, P.M., et al; "Comparison of Oral Capecitabine Versus Intravenous Fluorouracil Plus Leucovorin as First-Line Treatment in 605 Patients with Metastatic Colorectal Cancer: Results of a Randomized Phase III Study"; *Journal of Clinical Oncology*; vol. 19, No. 8; pp. 2282-2292 (2001).
Milgate, J., et al; "The Nutritional & Biological Significance of Saponins"; *Nutritional Research*; vol. 15 No. 8, pp. 1223-1249 (1993).
Guo, Z., et al; "Microwave-assisted extraction of effective constituents from a Chinese herbal medicine Radix puerariae"; *Analytica Chimica Acta*; vol. 436, pp. 41-47 92001).
Mimaki, Y., et al; "Steroidal Saponins from *Hosta Longipes* and Their Inhibitory Activity on Tumour Promoter-Induced Phospholipid Metabolism of HeLa Cells"; *Phytochemistry*, vol. 42, No. 4, pp. 1065-1070 (1996).
Australian Office Action; Examiner's first report on Patent Application No. 2004305302, dated Aug. 27, 2009 (2 pgs).
Chinese Office Action; Second Office Action on Patent Application No. 200480041735.3, dated Dec. 22, 2004, pp. 1-5.
Chinese Office Action; First Office Action on Patent Application No. 200680032400.4, dated Jul. 6, 2006, pp. 1-5.
Chinese Office Action; First Office Action on Patent Application No. 200680031670.3, dated Jul. 6, 2006, pp. 1-5.
Chinese Office Action; First Office Action on Patent Application No. 200480041735.3, dated Dec. 22, 2004, pp. 1-4.
British Search Report; Application No. GB0513888.8, Date of Search Nov. 1, 2005 (3 pgs).
British Search Report; Application No. GB0513881.3, Date of Search Nov. 1, 2005 (3 pgs).
Mexican Office Action; Application No. PA/a/2006/007087, dated Nov. 19, 2009 (2 pgs).
Gabor, M.; "Models of Acute Inflammation in the Ear"; *Methods in Molecular Biology*, vol. 225: Inflammation Protocols Edited by: P.G. Winyard & D.A. Willoughby © Humana Press Inc., Totowa, NJ; pp. 129-137 (2003).
Sauvaire, Y., et al; "Implication of Steroid Saponins and Sapogenins in the Hypocholesterolemic Effect of Fenugreek"; *LIPIDS* 26, 191-197 (1991).
Xu, X., et al; "Studies on saponin from seeds of *Trigonella foenum-graecum* (II) Isolation and structural elucidation for a new saponin A and its secondary glucosides"; *Chinese Traditional and Herbal Drugs*; p. 679 (2003).
Friedman, M., et al; "Effect of feeding solanidine, solasodine and tomatidine to non-pregnant and pregnant mice"; *Food and Chemical Toxicology*, vol. 41, pp. 61-71 (2003).
Skulina, C., et al; "Multiple sclerosis: Brain-infiltrating CD8$^+$T cells persist as clonal expansions in the cerebrospinal fluid and blood"; *PNAS*; vol. 101, No. 8; pp. 2428-2433 (2004).
Ley, K., et al; "Selectins in T-Cell Recruitment to Non-Lymphoid Tissues and Sites of Inflammation"; *Nature Reviews Immunology*; vol. 4, pp. 1-11 (2004).
Kim, S.Y., et al; "Inhibition of Mouse Ear Edema by Steroidal and Triterpenoid Saponins"; *Arch Pharm Res*, vol. 22, No. 3; pp. 313-316 (1999).
Confavreux, C., et al; "Age at disability milestones in multiple sclerosis"; *Brain*; vol. 129; pp. 595-605 (2006).
Confavreux, C., et al; "Natural history of multiple sclerosis: a unifying concept"; *Brain*, vol. 129; pp. 606-616 (2006).
Elovaara, I., et al; "Adhesion Molecules in Multiple Sclerosis"; *Arch Neurol*; vol. 57, pp. 546-551 (2000).
McDonnell, G.V., et al; "Serum soluble adhesion molecules in multiple sclerosis: raised sVCAM-1, sICAM-1 and sE-selectin in primary progressive disease"; *J. Neurol*; vol. 246; pp. 87-92 (1999).
Musso, A.M., et al; "Increased serum levels of ICAM-1, ELAM-1 and TNF-α in inflammatory disorders of the peripheral nervous system"; *Ital. J. Neurol. Sci.*; vol. 15; pp. 267-271 (1994).
Rao, A.V., et al; "The Bioactivity of Saponins: Triterpenoid and Steroidal Glycosides"; *Drug Metabolism and drug interactions*; vol. 17, No. 1-4; pp. 212-235 (2000).
Simmons, R.D., et al; "Sialyl ligands facilitate lymphocyte accumulation during inflammation of the central nervous system"; *Journal of Neuroimmunology*; vol. 41; pp. 123-130 (1992).
Ulbrich, H., et al; "Leukocyte and endothelial cell adhesion molecules as targets for therapeutic interventions in inflammatory disease"; *Trends in Pharmacological Sciences*; vol. 24, No. 12; pp. 640-647 (2003).
VanderElst, I.E., et al; "β1,6 N-Acetylglucosaminyltransferase (core 2 GlcNAc-T) expression in normal rat tissues and different cell lines: evidence for complex mechanisms of regulation"; *Glycobiology*, vol. 8, No. 7; pp. 731-740 (1998).
Washington, R., et al; "Expression of Immunologically Relevant Endothelial Cell Activation Antigens on Isolated Central Nervous System Microvessels from Patients with Multiple Sclerosis"; *Annals of Neurology*; vol. 35, No. 1; pp. 89-97 (1994).
Derwent Publications Ltd., London, GB AN 2001-412294 & JP 2001 072597 A (Mercian) Corp; Mar. 21, 2001; (abstract).
Davies, Michael J., et al; "The Expression of the Adhesion Molecules Icam-1, Vcam-1, Pecam, and E-Selectin in Human Atherosclerosis", *Journal of Pathology*, vol. 171: 223-239 (1993).
Ke, Hu et al; "The Cytotoxicity of Methyl Protoneogracillin (NSC-698793) and Gracillin (NSC-698787), Two Steroidal Saponins from the Rhizomes of *Dioscorea collettii* var. *hypoglauca*, against Human Cancer Cells in vitro"; *Phytother. Res.*; 17; 620-626 (2003).
Yu, Jing et al, "Progress in studies on chemical constituents and pharmacological effect of *Trigonella foenum-graecum*"; *Chinese Traditional and Herbal Drugs*, vol. 34, (12) 1146-1149 (2003).
Droogan A G et al "Serum and cerebrospinal fluid levels of soluble adhesion molecules in multiple sclerosis: predominant intrathecal release of vascular cell adhesion molecule-1"; Journal of Neuroimmunology 64 (1996) 185-191.
Shinya Hanashima et al "Systematic Synthesis of Bisubstrate-Type Inhibitors of *N*-Acetylglucosaminyltransferases" Chem. Eur. J. 2006, 12, 3449-3462.
Mohamed S Kamel et al, "Studies on Balanites aegyptiaca Fruits, an Antidiabetic Egyptian Folk Medicine"; Chemical & Pharmaceutica Bulletin 1991, 39(5), 1229-1233.
Takao Konoshima et al "Anti-Aids Agents, 21 Triterpenoid saponins as anti-HIV principles from fruits of gleditsia Japonica and gymnocladus chinesis and a structure-activity correlation"; Journ of Nat. Prods. vol. 58, No. 9, pp. 1372-1377, Sep. 1995.
Laurence A Lasky, "Selectin-Carbohydrate interactions and the initiation of the inflammatory response", Annual Review of Biochemistry 1995 vol. 64, pp. 113-139.
Daniel Lazarevia et al; "Artificial N-functionalised UDP-glucosamine analogues as modified substrates for *N*-acetylglycosaminyl transferases" Carbohydrate Research 2006, vol. 341(5), 569-576.
Hiromichi Matsuura; "Saponins in Garlic as Modifiers of the Risk of Cardiovascular Disease"; Journal of Nutrition 131, 1000S-1005S, 2001.
John G Ondeyka et al; "Discovery of structurally diverse natural product antagonists of chemokine receptor CXCR3"; Molecular Diversity (2005), 9, 123-129.
Carlo A Palmerini et al "An approach for fluorometric determination of glycosyltransferase activities", Glycoconjugate Journal (1996) 13, 631-636.
M M Vaghefi et al; "Synthesis of Glycopyranosylphosphonate Analogues of Certain Natural Nucleoside Diphosphate Sugars as Potential Inhibitors of Glycosyltransferases", Journal of Medicinal Chemistry, 1987, (30), 1383-1391.
M M Vaghefi et al, "Synthesis of certain nucleoside methylenediphosphonate sugars as potential INHIB", Journal of Medicinal Chemistry 1987, 30 1391-1399.

(56) References Cited

OTHER PUBLICATIONS

Co-pending CIP U.S. Appl. No. 11/980,727, filed Oct. 31, 2007.
Co-Pending U.S. Appl. No. 11/472,554, filed Jun. 22, 2006.
Co-Pending U.S. Appl. No. 10/584,470, filed Jun. 22, 2006.
Co-Pending U.S. Appl. No. 11/481,256, filed Jul. 6, 2006.
Chibber, R., et al; "Activity of the Glycosylating Enzyme, Core 2 GlcNAc (β,6) Transferase, is Higher in Polymorphonuclear Leukocytes From Diabetic Patients Compared With Age-Matched Control Subjects"; *Diabetes*; vol. 49; pp. 1724-1730 (2000).
Chibber, R., et al; "Protein Kinase C β2-Dependent Phosphorylation of Core 2 GlcNAc-T Promotes Leukocyte-Endothelial Cell Adhesion"; *Diabeties*; vol. 52; pp. 1519-1527 (2003).
Ellies, L.G., et al; "Core 2 Oligosaccharide Biosynthesis Distingjishes between Selectin Ligands Essential for Leukocyte Homing and Inflammation"; *Immunity*; vol. 9, pp. 881-890 (1998).
Goekjian, P.G., et al; "Protein kinase C inhibitors as novel anticancer drugs"; *Expert Opin. Investig. Drugs*; vol. 10, No. 12; pp. 2117-2140 (2001).
Hartung, Hans-Peter, MD; et al; "Circulating Adhesion Molecules and Tumor Necrosis Factor Receptor in Multiple Sclerosis: Correlation with Magnetic Resonance Imaging"; *Annals of Neurology*; vol. 38, No. 2; pp. 186-193 (1995).
Hindsgaul, O., et al; "Evaluation of Deoxygenated Oligosaccharide Acceptor Analogs as Specific Inhibitors of Glycosyltransferases"; *The Journal of Biological Chemistry*; vol. 266, No. 27; pp. 17858-17862 (1991).
Joshi, J., et al; "Chemistry of Ayurvedic Crude Drugs: Part VIII[a]-Shatavari-2: Structure Elucidation of Bioactive Shatavarin-I & other Glycosides[b,c]"; *Indian Journal of Chemistry*; vol. 27B; pp. 12-16 (1988).
Kim, S.Y., et al; "Inhibition of Mouse Ear Edema by Steroidal and Triterpenoid Saponins"; *Arch Pharm Res.*; vol. 22, No. 3, pp. 313-316 (1999).
Kuhns, W., et al; "Processing O-glycan core 1, Ga1β1-3GalNAca-R. Specificities of core 2, UDP-GlcNAc: Ga1β1-3GalNAc-R(GlcNAc to GalNAc) β6-N-acetylglucosaminyltransferase and CMP-sialic acid: Ga1131-3Ga1NAc-R α3-sialyltransferase"; *Glycoconjugate Journal*; vol. 10; pp. 381-394 (1993).
Matsuda, H., et al; "Protective Effects of Steroid Saponins from *Paris polyphylla* var. *yunnanensis* on Ethanol- or Indomethacin-Induced Gastric Mucosal Lesions in Rats: Structural Requirement for Activity and Mode of Action"; *Bioorganic & Medicinal Chemistry Letters*; vol. 13; pp. 1101-1106 (2003).
Orlacchio, A., et al; "Activity levels of a β1, 6 N-acetylglucosaminyltransferase in lymphomonocytes from multiple sclerosis patients"; *Journal of Neurological Sciences*; vol. 151; pp. 177-183 (1997).
Toki, D., et al; "Inhibition of UDP-G1cNAc:Ga1β1-3Ga1NAc-R (GlcNAc to GalNAc) β6-N-acetylglucosaminyltransferase from acute myeloid leukaemia cells by photoreactive nitrophenyl substrate derivatives"; *Biochemical and Biophysical Research Communications*; vol. 198, No. 2; pp. 417-423 (1994).
Washington, R., et al; "Expression of Immunologically Relevant Endothelial Cell Activation Antigens on Isolated Central Nervous System Microvessels from Patients with Multiple Sclerosis"; *Ann. Neurol*; vol. 35, No. 1; pp. 89-97 (1994).
Li, Cheng-Ming, et al; "Development of monoclonal antibodies against bovine mucin core β6 N-acetylglucosaminyltransferase"; *Glycoconjugate Journal*; vol. 16; pp. 555-562 (1999).
Rita Aquino et al, "Furostanol Oligosides from Tamus Communis", Journal of Natural Products vol. 49, No. 6, pp. 1096-1101, Nov.-Dec. 1986.
Jean-Guy Bienvenu et al, "Recombinant Soluble P-Selectin Glycoprotein Ligan- 1 -Ig Reduces Restenosis through Inhibition of Platelet-Neutrophil Adhesion after Double Angioplasty in Swine", *Circulation*. 27;103(8):1128-34 (2001).
Chen C. et al, *Yunnan Zhiwu Yanjiu*, 9(4), 495-502 (1987).
Chow F. et al., "Macrophages in streptozotocin-induced diabetic nephropathy: potenial role in renal fibrosis" Nephrol Dial Transplant. 19(12):2987-96 (2004).

Fujita S. et al , "Dammarane Glycosides from Aerial parts of Neoalsomitra Integrifoliola", *Phytochemistry*, 38(2), 465-72 (1995).
Guofeng Gu, et al , "Facile Synthesis of Saponins Containing 2,3-Branched Oligosaccharides by Using Partially Protecgted Glycosyl Donors", J. Org. Chem 2004, 69, 5497-5500.
Haladova M. et al., "Steroids saponins from the petals of Lilium candidum L.", *Pharmazie*, 54(2), 159-160 (1999).
Hansen A. et al., "Evaluation of Cardioprotective Effects Immunoglobulin in Myocardial Ischemia-Reperfusion of Recombinant Soluble P-Selectin Glycoprotein Ligan-Injury by Real-Time Myocardial Contrast Echocardiography" *J Am Coll Cardiol.* 18;44(4):887-91 (2004).
Hans-Peter Hartung et al, "Circulating Adhesion Molecules and Tumor Necrosis Factor Receptor in Multiple Sclerosis: Correlation with Magnetic Resonance Imaging" Ann Neurol 1995; 38(2), 186-193.
Hickey M. et al., "Leukocyte-Endothelial Cell Interactions are enhanced in Dermal Postcapillary Venules of MRL/fas[lpr] (Lupus-Prone) Mice: Roles of P- and E-Selectins[1]" *J Immunol.* 168(9):4728-36 (2002.
Haworth and Hirst, XXII—The Constitution of the Disaccharides. Part V, Vellobiose (Cellose)J. Chem. Soc. 119, 193 (1921).
Ke Hu et al, "Methyl protogracillin (NSC-698792): the spectrum of cytotoxicity against 60 human cancer cell lines in the National Cancer Institute;s anticancer drug screen panel", Anti-cancer Drugs 2001, 12, pp. 541-547.
Ke Hu et al "The Cytotoxity of Methyl Protoneogracillin (NSC-698793) and Gracillin (NSC-698787), Two Steroidal Saponins from the Rhizomes of *Dioscorea Collettii*var. hypoglauca, against Human Cancer Cells in vitro", Phytother. Res. 17, 620-626 (2003).
Ke Hu et al "Antineoplastic Agents; 11. Four Furostanol Glycosides from Rhizomes of *Dioscorea Collettii*var. *hypoglauca*", Planta Medica 63 (1997) 161-165.
Hurwitz AA et al "Tumor Necrosis Factor a Induces Adhesion Molecule Expression on Human Fetal Astrocytes", J. Exp. Med, 1992 vol. 176, Dec. 1992 pp. 1631-1636.
Kentaro Inoue et al, "Purification and characterization of furostanol glycoside 26-O-β-glucosidase from *Costus speciosus* rhizomes", FEDS Letters, 278 (1996) pp. 157-160.
Inoue T. et al., "Blockade of PSGL-1 attenuates CD14 +monocytic cell recruitment in intestinal mucosa and ameliorates ileitis in SAMP1/Yit mice", *J Leukoc Biol.* 77(3):287-95 (2005).
Kessar S. et al., "Synthetic Studies in Steroidal Sapogenins and Alkaloids-III" *Tetrahedron*. 24(2):887-92 (1968).
Kessar S et al., "Synthetic Studies in Steroidal Sapogenins and Alkaloids-V", Tetrahedron vol. 24, pp. 899-904 (1968).
Kessar S et al., "Synthetic Studies in Steroidal Sapogenins and Alkaloids-VI", Tetrahedron vol. 24, pp. 905-907 (1968).
Ravindra Kumar et al., "Core 1β-1,6-N-Acetylglucosaminyltransferase Enzyme Activity is Critical for P-Selectin Glycoprotein Ligand-1 Binding to P-Selectin", Blood, vol. 88, No. 10, pp. 3872-3879 (1996).
Martina Lahmann et al.," a facile approach to diosgenin and furostan type saponins bearing a 3β-chacotriose moiety"., Carbohydrate Research 337 (2002) 2153-2159.
Marion Lanteri et al., "Altered T cell surface glycosylation in HIV-1 infection results in increased susceptibility to galectin- 1-induced cell death", Glycobiology vol. 13, No. 12, pp. 909-918 (2003).
Sohpie Lautrette et al., "A new method of solvent free O- and N-glycosylation using activated carbon fiber 9ACF) as a promoter. Application to the synthesis of saponin and nucleoside analogues", Chem Commun. (2004) pp. 586-587.
Chuan Li et al., "Synthesis of diosgenyl α-L-rhamnopyransoy1-(1→2)-[β-D-glycopyranosyl-(1→3)]-β-D-glucopyranoside (gracillin) and related saponins", Carbohydrate Research 306 (1998) 189-195.
Ming Li et al., "Synthesis of monomethylated dioscin derivatives and their antitumor activities", Carbohydrate Research 338 (2003) 117-121.
Liu C. et al, Yaoxue Xuebao, (1983) vol. 18, p. 8 pp. 597-606.
Hongwei Liu et al ., "Two new Pregnane Glycosides from *Dioscorea futschauensis* R. Kunth"., Chem. Pharm. Bull. 51(9) 1089-1091 (2003).

(56) References Cited

OTHER PUBLICATIONS

Robert W McMurray et al., "Adhesion Molecules in Autoimmune Disease"., Semin. Arthritis and Rheumatism vol. 25, No. 4, Feb. 1996, pp. 215-33.
Yoshihiro Mimaki et al., "Steroidal Saponins from the bulbs of *Lilium Regale and L. Henryl*"., Phytochemistry, vol. 33 No. 3 pp. 675-682, 1993.
Yoshihiro Mimaki et al., "Steroidal Saponins from the bulbs of *Lilium Longiglorum* and their antitumour-promoter activity"., Phytochemistry, vol. 37, No. 1 pp. 227-232 (1994).
Yoshihiro Mimaki et al., "New Steroidal Constituents from the Bulbs of *Lilium candidum*", Chem. Pharm. Bull 46 (11) 1829-1832 (1998).
Daniel Myers, et al., "New and Effective Treatment of Experimentally Induced Venous Thrombosis with Anti-inflammatory rPSGL-lg", Throm Haemost 2002, 87, 374-82.
Osamu Nakamura, et al., "Steroidal Saponins from the Bulbs of *Lilium Speciosum x L. Nobilissimum* 'Star Gazer' and their antitumour-promoter activity", Phytochemistry, vol. 36, No. 2, pp. 463-467 (1994).
Kenji Oda et al., "Adjuvant and Haemolytic Activities of 47 Saponins Derived from Medicinal and Food Plants"., Biol. Chem. vol. 381, pp. 67-74, Jan. 2000.
Kazutomo Ori et al., "Jatropham Derivatives and steroidal saponins from the Bulbs of *Lilium HansonII*"., Phytochemistry., vol. 31, No. 8, pp. 2767, 2775, (1992).
Jean-Hugues Renault et al., "Dammarane Saponins from *Zizyphus lotus*", Phytochemistry vol. 44, No. 7., pp. 1321-1327 (1997).
Emile M. Rijcken et al , "Immunoblockade of PSGL-1 attenuates established experimental murine colitis by reduction of leukocyte rolling", Am J Physiol 287, G115-G124, (2004).
Shengmin Sang et al., "Furostanol saponins from *Allim tuberosum*"., Phytochemistry 52 (1999) pp. 1611-1615.
Serban C Stoica et al., "Endothelial Activation in the Transplanted Human Heart from Organ Retrieval to 3 months after Transplantation: An Observational Study", J. Heart Lung/Transplant., 24(5) 593-601 (2005).
Hostettmann, K. et al; Chemistry and pharmacology of natural products; Saponins Cambridge University Press (1995) (extracted book pages).
Erich C Strauss et al ., "Soluble P-Selectin Glycoprotein Ligand 1 Inhibits Ocular Inflammation in a Murine Model of Allergy", Invest Ophthalmol/Vis Sci. 40(7); 1336-421 (1999).
Jean-Francois Tanguay et al., "Prevention of in-stent restenosis via reduction of thrombo-inflammatory reactions with recombinant P-selectin glycoprotein ligand-1", thromb Haemost 2004, 91, 1186-93.
Akihiko Tobari et al, "Spirostanols obtained by cyclization of pseudosaponin derivatives and comparison of anti-platelet agglutination activities of spirostanol glycosides", Eur. J. Med. Chem 35 (2005) 511-527.
M. Tomova et al., "Steroidal Saponins from Tribulus Terrestris L. with a Stimulating Action on the Sexual Functions", Int. Conf. Chem Biotechnol (1981), 3, 1, 298-302.
I. S Vail'eva et al., "Steroid Saponins from Rhizomes of the Caucasian Yam", Pnkl. Biochim Mikrobiol (1984) 20(3) p. 330-332.
Kai Wang et al., "Recombinant Soluble P-Selectin Glycoprotein Ligand-lg (rPSGL-1g) Attenuates Infarct Size and Myeloperoxidase Activity in a Canine Model of Ischemia-Reperfusion", Thromb Haemost (2002) 88, 149-54.
Shao-Min Wang et al., "Syntheses of acetylated steroid glycosides and selective cleavage of O-acetyl groups in sugar moiety", Steroids 69 (2004) 599-604.
Tadayuki Yago et al., "Structurally Distinct Requirements for Binding of P-selectin Glycoprotein Ligand-1 and Sialyl Lewis x to *Anaplasma phagocytophilum* and P-selectin", J. Biol Chem. (2003) vol. 278, No. 39, 37987-37997.
Deng-Jye Yang et al., "Isolation and Identification of Steroidal Saponins in Taiwanese Yam Cultivar (Dioscorea pseudojaponica Yamamoto", J. Agric. Food Chem. (2003) 51, 6438-6444.

Feng Yin et al., "Dammarane-Type Glycosides from *Gynostemma pentaphyllum*", J. Nat. Prod. (2004) 67 pp. 942-952.
Kazuko Yoshikawa et al., "Antisweet Natural Products. VII. Hodulosides I, II, III, IV and V from the Leaves of Hovenia dulcis THUNB", Chem Pharm. Bull. 40(9) 2287-2291 (1992).
Kazuko Yoshikawa et al.,"Antisweet Natural Products. VI. Jujubasaponins IV, V and VI from *Zizyphus jujube mill.*", Chem. Pharm. Bull. 40(9) 2275-2278 (1992).
Qing-An Zheng et al., "Steroidal saponins from fresh stem of *Dracaena Cochinchinensis*", Steroids 69 (2004) 111-119.
PCT Notification of Transmittal of the International Search Report and the Written Opinion of the International Searching Authority, or the Declaration; International Application No. PCT/GB2004/005398, filed Dec. 22, 2004; Applicant's or agent's file Reference No. 500496WO01; May 31, 2005.
Cheng, M.S., et al; "Total Synthesis of Methyl Protodioscin: A Potent Agent with Antitumor Activity"; J. Org. Chem.; vol. 68; pp. 3658-3662 (2003); Citation May 31, 2005; XP-002328851.
Ravikumar, P.R., et al; "Chemistry of Ayurvedic Crude Drugs: Part VI$^a$-(Shatavari-1): Structure of Shatavarin-IV$^{b,c}$"; *Indian Journal of Chemistry*; vol. 26B, pp. 1012-1017 (1987); Citation May 31, 2005; XP-001096221.
Toki, D., et al; "Inhibition of UDP-GlcNAc:Ga1131-3Ga1NAc-R (GlcNAc to GalNAc) β6-N-acetylglucosaminyltransferase from acute myeloid leukaemia cells by photoreactive nitrophenyl substrate derivatives"; *Biochemical and Biphysical Research Communications*; vol. 193, No. 2; pp. 417-423 (1994); Citation May 31, 2005; XP002922997.
Yoshikawa, M., et al; "Medicinal Foodstuffs. VIII. Fenugreek Seed. (2) : Structures of Six New Furostanol Saponins, Trigoneosides IVa, Va, Vb, VI, VIIb, and VIIIb, From the Seeds of Indian *Trigonella Foenum-Graecum L.*"; Heterocycles, vol. 47, No. 1; pp. 397-405 (1998); Citation May 31, 2005; XP-001205771.
PCT Notification of Transmittal of the International Search Report and the Written Opinion of the International Searching Authority, or the Declaration; International Application No. PCT/GB2006/002301, filed Jun. 22, 2006; Applicant's or agent's file Reference No. 500966WO01 Nov. 15, 2006.
Orlacchio, A., et al; "Activity levels of a β1,6 N-acetylglucosaminyltransferase in lymphomonocytes from multiple sclerosis patients"; *Journal of the Neurological Sciences*; vol. 151; pp. 177-183 (1997); Citation Nov. 15, 2006; XP-002232475.
PCT Notification of Transmittal of the International Search Report and the Written Opinion of the International Searching Authority, or the Declaration; International Application No. PCT/GB2006/002500, filed Jul. 6, 2006; Applicant's or agent's file Reference No. 500964WO01 May 25, 2007.
Derwent Publications Ltd., London, GB; AN 2003-664094 & CN 1 415 625 A (Jilin Tianyao Sci & Technology Co. Ltd) May 7, 2003; Citation May 25, 2007; (Abstract) XP-002433233.
Derwent Publications Ltd., London, GB; AN 2001-412294 & JP 2001 072597 A (merican Corp); Mar. 21, 2001; Citation May 25, 2007; (Abstract) XP-002433234.
Derwent Publications Ltd., London, GB; AN 2000-476485 & CN 1 243 129 A (Univ. Shenyang Medicine); Feb. 2, 2000; Citation May 25, 2007; (Abstract) XP-002433235.
Hu, K., et al; "The Cytotoxicity of Methyl Protoneogracillin (NSC-698793) and Gracillin (NSC-698787), Two Steroidal Saponins from the Rhizomes of *Dioscorea collettii* var. *hypoglauca*, against Human Cancer Cells in vitro"; *Phytother. Res.*, vol. 17, pp. 620-626 (2003); Citation May 25, 2007.
Aquino, R., et al; "Antiviral Activity of Constituents of *Tamils communis*"; *Journal of Chemotherapy*; vol. 3, No. 5; pp. 305-309 (1991); Citation May 25, 2007.
Baek, S.H., et al; "Inactivation of Human Pleural Fluid Phospholipase A$_2$ by Dioscin"; *Arch. Pharm. Res.*; vol. 17, No. 4; pp. 218-222 (1994); Citation May 25, 2007.
Ondeyka, J.G., et al; "Discovery of structurally diverse natural product antagonists of chemokine receptor CXCR3"; *Molecular Diversity*; vol. 9; pp. 123-129 (2005); Citation May 25, 2007.
Sautour, M., et al; "Antifungal steroid saponins from Dioscorca caycncnsis. Plant Medica;" *Antimicrobial Activity*; vol. 70(1); pp. 90-92 (2004); Citation May 25, 2007.

(56) References Cited

OTHER PUBLICATIONS

PCT Notification of Transmittal of the International Search Report and the Written Opinion of the International Searching Authority, or the Declaration; International Application No. PCT/GB2006/002518, filed Jul. 6, 2006; Applicant's or agent's file Reference No. 500965WO01; Dec. 19, 2006.
Derwent Publications Ltd., London, GB; AN 2004-239758; Huang, H., et al; "Medicine composition for treating myocardial ischemia, angina pectoris and cardiac infraction"; & CN 1 465 344 A (Chengdu Diao Pharm Group Co Ltd) Jan. 7, 2004 (Abstract) XP-002409228; Citation Dec. 19, 2006.
Derwent Publications Ltd., London, GB; AN 2005-426073; Wang Jingang; "Dioscin oral disintegration tablet and its preparing method"; & CN 1 586 493 A (Kexinbicheng Medicine Science) Mar. 2, 2005 (Abstract) XP-002409229; Citation Dec. 19, 2006.
Derwent Publications Ltd., London, GB; AN 2002-751531; Zhu Dayuan et al; "Furost saponine analogue and its separatin process and use" & CN 1 184 229 C (Shanghai Inst of Pharmacology) Jan. 12, 2005 (Abstract) XP-002409230; Citation Dec. 19, 2006.
Derwent Publications Ltd., London, GB, AN 2005-631469; Han J. et al; "Medicine for regulating blood fat and treating cardiocerehral disease and preparing method"; & CN 1 615 896 A (Yunnan Prov Medicine Inst) May 18, 2005 (Abstract) XP-002409231; Citation Dec. 19. 2006.
Derwent Publications Ltd., London, GB, AN 2000-443110; Li Pingya et al; "Process for extracting ginsenoside Re, and use of medicine thereof"; & CN 1 242 374 A (Xinliheng Pharmaceutical Scien) Jan. 26, 2000; (Abstract) XP-002409232; Citation Dec. 19, 2006.
Derwent Publications Ltd., London, GB, AN 1998-087548; Junpeng Peng et al; "Anti-thrombosis glucoside medicine"; & CN 1 138 984 A (Radiomedicine Inst Military ME) Jan. 1, 1997; (Abstract) XP-002409233; Citation Dec. 19, 2006.
Derwent Publications Ltd., London, GB, AN 2006-272298; Fu T., et al; "Steroidal saponin pharmaceutical composition, its preparation method and use"; & WO 2006/034655 a (chengdu Diao Pharm Group Co Ltd) Apr. 6, 2006 (Abstract) XP-002409234; Citation Dec. 19, 2006.
Zhang, J., et al; "Effect of six steroidal saponins isolated from anemarrhenae rhizome on platelet aggregation and hemolysis in human blood"; *Clinica Chimica Acta*; vol. 289; pp. 79-88 (1999); Citation Dec. 19, 2006.
S. Akhov et al.2000, Biological Activity of Deltoside from *Allium Nutans* L. In Saponins in Food, Feedstuffs and Medicinal Plants edited by W Oleszek and A Marston.
Bernadete P. da Silva, et al, A New Bioactive Steroidal Saponin from *Agave attenuata*; Z. Naturforsch, 57c, 423-428 (2002).
Mei Dong et al, Two New Steroidal Saponins from the Rhizomes of Dioscorea panthaica and their Cytotoxic Activity; Planta Med. 67 (2001) 853-857.
M. Dong et al, Steroidal saponins from Dioscorea panthaica and their cytotoxic activity; Pharmazie 59, 294-296 (2004).
B. B. Gaitonde et al; Antioxytocic action of Saponin isolated from Asparagus Racemosus Willd (Shatavari) on Uterine Muscle; Arch. int. Pharmacodyn., 1969, 179, No. 121-129.
Antonio G. Gonzalez et al; Steroidal Saponins from the Bark of Dracaena draco and Their Cytotoxic Activities; J. Nat. Prod. 2003, 66, 793-798.
Juan C. Hernandez et al, Icogenin, a new cytotoxic steroidal saponin isolated from *Dracaena draco*; Bioorganic & Medicinal Chemistry 12 (2004) 4423-4429.
Hiroschige Hibasami et al, Protodioscin isolated from fenugreek (*Trigonella foenumgraecum L*). induces cell death and morphological change indicative of apoptosis in leukemic cell line H-60, but not in gastric cancer cell line KATO III; International Journal of Molecular Medicine 11: 23-26, 2003.
Ke Hu et al; Methyl protogracillin (NSC-698792): the spectrum of cytotoxicity against 60 human cancer cell lines in the National Cancer Institute's anticancer drug screen panel, Anti-Cancer Drugs 2001, 12, pp. 541-547.

M. A. Lacaille-Dubois et al; a review of the biological and pharmacological activities of saponins: Phytomedicine vol. 2(4), pp. 363-386, 1996.
H.W. Liu et al; Bioactive saponins from Dioscorea futschauensis: Pharmazie 57 (2002) 8 570-572.
Yoshihiro Mimaki et al; Steroidal Saponins from the bulbs of *Triteleia Lactea* and their inhibitory activity on cyclic amp phosphodiesterase: Phytochemistry, vol. 38, No. 5, pp. 1279-1286, 1995.
Yoshihiro Mimaki et al; Cytotoxic Activities and Structure-Cytotoxic Relationships of Steroidal Saponins: Biol. Pharm. Bull, 24(11) 1286-1289 (2001).
Pierre R Petit et al; Steroid saponins from fenugreek seeds: Extraction, purification, and pharmacological investigation on feeding behaviour and plasma cholesterol: Steroids, 60: 674-680, 1995.
P. Sur et al; Short Communication Trigonella foenum graecum (Fenugreek) Seed Extract as an Antineoplastic Agent: Phytotherapy Research, 15, 257-259 (2001).
Yi-Fei Wang et al; Inhibitory Effects of Some Steroidal Saponins on Human Spermatozoa in vitro: Planta Medica 62 (1996) 130-132.
Ethan Basch et al; Therapeutic Applications of Fenugreek: Alternative Medicine Review vol. 8, No. 1, 2003 pp. 20-27.
Dinesh Puri; Therapeutic Potentials of Fenugreek: Indian J Physiol Pharmacol. 1998; 42(3) pp. 423-424.
L. S. Akhov et al Structure of Steroidal Saponins from Underground Parts of *Allium nutans L.*; J. Agric. Food Chem. 1999, 47, 3193-3196.
Paul V. Beaum et al; Expression of Core 2 $\beta$-1,6-$N$-Acetylglucosaminyltransferase Line Results in Altered Expression of MUC1 Tumor-associated in a Human Pancreatic Cancer Cell Epitopes; The Journal of Biological Chemistry, vol. 274, No. 35, Issue of August 27, pp. 24641-24648, 1999.
Christopher Broca et al; 4-Hydroxyisoleucine: effects of synthetic and natural analogues on insulin secretion; European Journal of Pharmacology 390 (2000) 339-345.
I. Brockhausen et al; Biosynthesis of *O*-Glycans in Leukocytes from Normal Donors and from Patients with Leukemia: Increase in *O*-Glycan Core 2 UDP-G1cNAc:Gal$\beta$3GalNAc$\alpha$-R(GlcNAc to GalNAc)$\beta$(1-6)-$N$-Acetylglucosaminyltransferase in Leukemic Cells; Cancer Research 51, 1257-1263, Feb. 15, 1991.
Mao S. Cheng et al; Total Synthesis of Methyl Protodioscin: a Potent Agent with Antitumor Activity; J.Org.Chem. 2003, 68, 3658-3662.
Karen J. Colley; Golgi localization of glycosyltransferases: more questions than answers; Glycobiology vol. 7, No. 1 pp. 1-13, 1997.
Martin Dalziel et al; the Relative Activities of the C2GnT1 and ST3Gal-I Glycosyltransferases Determine *O*-Glycan Structure and Expression of a Tumor-associated Epitope on MUCI; The Journal of Biological Chemistry Vo. 276, No. 14, Issue of April 6, pp. 11007-110015, 2001.
Matthew D. Davis et al, Diabetic Retinopathy; Diabetes Care, vol. 15, No. 12, Dec. 1992, pp. 1844-1874.
Michael J. Davies et al; The expression of the adhesion molecules ICAM-1, VCAM-1, PECAM, and E-Selectin in Human Atherosclerosis; Journal of Pathology, vol. 171, 223-229 (1993).
Shaojiang Deng et al; Synthesis of three diosgenyl saponins: dioscin, polyphyllin D, and balanitin 7; Carbohydrate Research 317 (1999) 53-62.
Yuguo Du et al; Synthesis of Saponins Using Partially Protected Glycosyl Donors; Organic Letters 2003, vol. 5, No. 20, 3627-3630.
Umit Guray et al; Levels of Soluble adhesion molecules in various clinical presentations of coronary atherosclerosis; International Journal of Cardiology 96 (2004) 235-240.
Umit Guray et al; Poor coronary collateral circulation is associated with higher concentrations of soluble adhesion colecules in patients with single-vessel desease; Coronary Artery Disease 2004, 15: 413-417.
Ronald Klein et al; The Wisconsin Epidemiologic Study of Diabetic Retinopathy: X. Four-Year Incidence and Progression of Diabetic Retinopathy When Age at Diagnosis is 30 years or More; Arch Ophthalmol 1989; 107: 244-249.
Eva M. Kohner et al; Diabetic Retinopathy in Diabetic Angiopathy, Tooke J.E., pp. 233-247, Oxford University Press (1999).

(56) References Cited

OTHER PUBLICATIONS

Daisuke Koya et al; Perspectives in Diabetes: Protein Kinase C Actibvation and the Development of Diabetic Complications; Diabetes, vol. 47, 859-866, 1998.

Diasuke Koya et al; Overexpression of core 2, N-acetylglycosaminyltransferase enhances cytokine actions and induces hypertrophic myocardium in transgenic mice: FASEB J. 13, 2329-2337 (1999).

Kensuke Kumamoto et at; Specific Detection of Sialyl Lewis X Determinant Caned on the Mucin GlcNAcβ1→6GalNAcα Core Structure as a Tumor-Associated Antigen; Biochemical and Biophysical Research Communications 247, 514-517 (1998).

Suzanne Laferte et al; Glycosylation-dependent Collagen-binding Activities of Two Membrane Glycoproteins in MDAY-D2 Tumor Cells: Cancer Research 48, 4743-4748, Sep. 1, 1988.

Chuan Li, et al; Synthesis of Diosgenyl α-L-rhamnopyranosyl-(1→2)—[β-D-glucopyranosyl-(1→3)]-β-D-glucopyranoside (gracillin) and related saponins; Carbohydrate Research 306 (1998) 189-195.

Bing Li et al; An improved synthesis of the saponin, polyphyllin D; Carbohydrate Research 331 (2001) 1-7.

Emi Machida et al; Clinicopathological Significance of Core 2 β,6-N-Acetylglucosaminyltransferase Messenger Rna Expressed in the Pulmonary Adenocarcinoma Determined by in situ hybridization; Cancer Research 61, 2226-2231, Mar. 1, 2001.

Marja-Leena Majuri et al; Recombinant E-selectin-protein mediates tumor cell adhesion via sialyl-Lea and sialyl-Lex; Biochemical and Biophysical Research Communications, vol. 182, No. 3 1992, Feb. 14, 1992, pp. 1376-1382.

Matthias Meier et al; Protein kinase C activation and its pharmacological inhibition in vascular disease; Vascular Medicine 2000; 5: 173-185.

Yoshihiro Mimaki et al; Steroidal Saponins and Alkaloids from the Bulbs of Lilium brownie var. colchesteri; Chem. Pharm. Bull 38(11) 3055-3059 (1990).

N T Mulvihill et al ; Inflammation in acute coronary syndromes; Heart 2002, 87, 201-204.

Toshiyuki Murakami et al; Medicinal Foostuffs. XVII. Fenugreek Seed. (3): Structures of New Furostanol-Type Steroids Saponins, Trigoneosides Xa, Xb, XIb, XIIa, XIIb, and XIIIa, from the Seeds of Egyptian Trigonella Foenum-graecum L; Chem. Pharma. Bull. 48(7)1994 1000 (2000).

Mitsuru Nakamura et al; Simultaneous core 2 β→6N-acetylglycosaminyltransferase up-regulation and sialyl-Le expression during activation of human tonsillar B lymphocytes; FEBS Letters 463 (1999) 125-128.

Yoshihiko Nishio et al; Identification and Characterization of a Gene Regulating Enzymatic Glycosylation which is Induced by Diabetes and Hyperglycemia Specifically in Rat Cardiac Tissue; J. Clin. Invest. vol. 96, Oct. 1995, 1759-1767.

Kevin D O'Brien et al; Neovascular Expression of E-Selectin, Intercellular Adhesion Molecule-1, and Vascular Cell Adhesion Molecule-1 in Human Atherosclerosis and Their Relation to Intimal Leukocyte Content; 1996 American Heart Association, In.c. 1996; 93: 672-682.

Katsuyuki Ohmori et al; A Distinct Type of Sialyl Lewis X Antigen Defined by a Novel Monoclonal Antibody is Selectively Expressed on Helper Memory T Cells; Blood, vol. 82, No. 9 (November 1); 1993 pp. 2797-2805.

Hans Paulsen et al; Synthese von modifizierten Derivaten des Disaccharides β-D-Gal-(1→3)-α-D-GalNAc zur Untersuchung der Substratspezifitat der Core-2-β-GlcNAc-Transferase and α-3-Sialyltransferase der Biosynthese von O-Glycoproteinen: Liebigs Ann. Chem. 1992, 747-758.

George R Pettit et al: Isolation and Structure of Cytostatic Steroidal Saponins from the African Medicanal Plant Balanites Aegyptica; Journal of Natural Products Vo. 54, No. 6 pp. 1491-1502 Nov.-Dec. 1991.

Friedrich Piller et al; Human T-lymphocyte Activation is Associated with changes in O-Glycam Biosynthesis; The Journal of Biological Chemistry, vol. 263, No. 29, Issue of October 15, pp. 15146-15150, 1988.

Jutta Renkonen et al; Core 2 β,6-N-acetylglycosaminyltransferases and α1,3-fucosyltransferases regulate the synthesis of O-glycans on selectin ligands on oral cavity carcinoma cells; APMIS 109, 500-6, 2001.

P. R. Ravikumar et al; Chemistry of Ayurvedic Crude Drugs: Part VI-(Shatavari-1):Structure of Shatavarin-IV; Indian Journal of Chemistry vol. 26B, Nov. 1987, pp. 1012-1017.

Osamu Saitoh et al; Expression of Aberrant O-Glycans attached to Leukosialin in Differentiation-deficient Hl-60 Cells; Cancer Research 51, 2854-2862, Jun. 1, 1991.

Yutaka Sashida et al; Studies on the Chemical Constituents of the Bulbs of Lilium mackliniae; Chem. Pharm. Bull. 39 (9) 2362-2368 (1991).

Yves Sauvaire et al; 4-Hydroxyisoleucine. A novel amino acid potentiator of insulin secretion; Diabetes, vol. 47, Feb. 1998 pp. 206-210.

S C Sharma et al; Oligofurostanosides from Asparagus Curillus leaves; Phytochemistry, Vo. 33, No. 3, pp. 683-686, 1993.

R D Sharma et al; Effect of fenugreek seeds on blood glucose and serum lipds in Tyupe 1 diabetes; European Journal of Clinical Nutrition (1990) 44, 301-306.

Kazuhisa Shimodaira et al; Carcinoma-associated Expression of Core 2 β-1,6-N-Acetylglucosaminyltransferase Gene in Human Colorectal Cancer: Role of O-Glycans in Tumor Progression; Cancer Research 57, 5201-5206 Dec. 1, 1997.

Hiroko Shimomura et al; Steroidal Saponins, PardarinosideA-G from the Bulbs of Lilium Pardarinum; Phytochemistry, Vo. 28, No. 11 pp. 3163-3170, 1989.

Markus Sperandio et al; Severe impairment of leukocyte rolling in venules of core 2 glyucosaminyltransferase-deficient mice; Blood, Jun. 15, 2001, vol. 97. No. 12, pp. 3812-3819.

Akiko Takada et al; Contribution of Carbohydrate Antigens Sialyl Lewis A and Sialyl Lewis X to Adhesion of Human Cancer Cells to Vascular Endothelium; Cancer Research 53, 354-361, Jan. 15, 1991.

Shigeru Tsuboi et al; Branched O-linked oligosaccharides ectopically expressed in transgenic mice reduce primary T-cell immune responses; The EMBO Journal vol. 16, No. 21, pp. 6364-6373, 1997.

Shigeru Tsuboi et al; Overexpression of Branched O-Linked Oligosaccharides on T Cell Surface Glycoproteins Impairs Humoral Immune Responses in Transgenic Mice; The Journal of Biological Chemistry Vo. 273, No. 46, Issue of Nov. 13, pp. 30680-30687, 1998.

Shigeru Tsuboi et al; Roles of O-linked oligosaccharides in immune responses; BioEssays 23:46-53, 2001.

Ajit Varki; Special Invited Review: Biological roles of oligosaccharides: all of the theories are correct; Glycobiology Vo. 3, No. 2 pp. 97-130, 1993.

I.S.Vasil'eva et al; Composition and Biological Activity of Steroid Glycosides from Cell Suspensions of Discorea deltoidea Wall; Applied Biochemistry and Microbiology, vol. 31, No. 2, 1995 pp. 206-209.

Gerd Walz et al; Recognition by ELAM-1 of the Sialyl-Le Determinant on Myeloid and Tumor Cells; Science, vol. 250 pp. 1132-1135, 1990.

Patricia P Wilkins et al; Structures of the O-Glycans on P-selectin Glycoprotein Ligand-1 from HL-60 Cells; the Journal of Biological Chemistry, vol. 271, No. 31, Issue of Aug. 2, pp. 18732-18742, 1996.

David Williams et al; Detection in Canine Submaxillary glands of an N-Acetylglucosaminyltransferase which acts on mucin substrates; The Journal of Biological Chemistry, Vol . 255, No. 23, Issue of December 10, pp. 11247-11252, 1980.

Masayuki Yoshikawa et al; Medicinal Foodstuffs IV. Fenugreek Seed. (1): Structures of Trigoneosides Ia, Ib, IIa, IIb, IIIa and IIIb, New Furostanol Saponins from the Seeds of Indian Trigonella Foenum-graecum L; Chem. Pharm. Bull. 45(1) 81-87 (1997).

Masayuki Yoshikawa et al; Medicinal Foodstuffs, VIII. Fenugreek Seed (2): Structures of six new Furostanol Saponins Trigoneosides IVa, Va, Vb, Vi, VIIb, and VIIIb, from the Seeds of Indian Trigonella Foenum-Graecum L.; Heterocycles, vol. 47, No. 1, 1998, pp. 397-405.

(56) References Cited

OTHER PUBLICATIONS

Shida Yousefi et al; Increased UDP-GlcNAc:Galβ1-3GalNAc-R (GlcNAc to GalNAc) α-1, 6-*N*-Acetylglucosaminyltransferase Activity in Metastatic Murine Tumor Cell Lines; The Journal of Biological Chemistry, vol. 266, No. 3, Issue of January 25, pp. 1772-1782, 1991.
Biao Yu, A "Double Random" Strategy for the Preparation of Saponin Libraries; J. Comb. Chem. 2001, 3, 404-406.
Biao Yu et al; The first synthetic route to furostan saponins; Tetrahedron Letters 42 (2001) pp. 77-79.
Biao Yu, et al; Glycosyl Trifluoroacetimidates.2. Synthesis of Dioscin and Xiebai Saponin 1; J. Org Chem. 2002, 67, 9099-9102.
Robert A Moreau et al; Phytosterols, phytostanols, and their conjugates in Foods: structural diversity, quantitative analysis, and health-promoting uses; Progress in Lipd Research 41, (2002) 457-500.
Garai, S. ,et al; Bacopasaponin D-A Pseudojujubogenin Glycoside from *Bacopa Monniera*; Phytochemistry, vol. 43, No. 2, pp. 447-449 (1996).
Hosny, M., et al; Balanitoside, A furostanol Glycoside, and 6-Methyl-Diosgenin from *Balanites Aegyptiaca*, Phytochemistry, vol. 31, No. 10 pp. 3565-3569 (1992).
Hostettmann, K., et al; Saponins (Chemistry and Pharmacology of Natural Products), Cambridge University Press, Cambridge, UK, Extract (1995).
Kim, H., et al; Chemical Synthesis of 15-Ketosterols and their Inhibitions of Cholesteryl Ester Transfer Protein: Bioorganic & Medicinal Chemistry, vol. 3, No. 4, pp. 367-374 (1995).
Mimaki, Y., et al; Steroidal Saponins from the Bulbs of *LILIUM BROWNII*: Phytochemistry, vol. 29, No. 7, pp. 2267-2271 (1990).
Miyahara, K., et al; Conversion of Steroid Saponins to the Corresponding Pregnane Glycosides: Chem. Pharm. Bull. 20 (11) 2506-2510 (1972).
Mori, K., et al; Synthesis of some analogues of Blattellastanoside A, the Steroidal Aggregation Pheromone of the German Cockroach: Bioorganic & Medicinal Chemistry, vol. 4, No. 3, pp. 401-408 (1996).
On, K., et al; Norlanostane and Lanostane Glycosides from the Bulbs of *Chionodoxa Luciliae* and Their Cytotoxic Activity; Chem. Pharm. Bull 51 (1) 92-95 (2003).
Takahashi, T., et al; Increased Spontaneous Adherence of Neutrophils from Type 2 Diabetic Patients with Overt Proteinuria; Diabetes Care, vol. 23, No. 3 pp. 417-418 (2000).
Tribosten wrapper—box from sample of a protodioscin containing extract sold by Thermolife International, purchased on-line (2003).
Vasil'eva, et al; Steroid Glycosides from Suspension Cultures of *Dioscorea Deltoidea Cells and Their Biological Activity in "Saponins used in Traditional and Modern Medicine" Eds Waller and Yamasaki*, Plenum Press New York (1996).
Yamishita, T., et al; Structures of three new steroidal alkaloid glycosides m solaverines I, II and III from Solanum Toxicarium and S. Verbascifolium; Chem. Pharm. Bull. 38 (3) pp. 827-829 (1990).
Yang, X., et al; The effect of TNF-α on glycosylation pathways in bovine synoviocytes; Biochem. Cell Biol. 82 pp. 559-568 (2004).
Belozerskaya V, et al, Effect of steroid glycosides on *Neurospora crassa* Membranes; Applied Biochemistry and Microbiology, vol. 30, No. 6 1994 pp. 724-728.
Brockhausen I et al; The separation of liquid chromatography (under elevated pressure) of phenyl, benzyl, and $_o$-nitrophenyl glycosides of oligosaccharides. Analysis of substrates and products for four *N*-acetyl $_D$-Glucosaminyl-transferases involved in mucin synthesis; Carbohydrate Research, 120(1983) pp. 3-16.
Brower Thomas D et al; Rheumatoid Arthritis; Journal of the Kentucky Medical Association, May 1983, pp. 281-286.
Chiang HC et al Xanthine Oxidase Inhibitors from the Roots of Eggplant (Solanum melongena L), J. Enzyme Inhibition 1993, vol. 7, pp. 225-235.
Deepak M et al., Quantitative Determination of the Major Saponin Mixture Bacoside A in *Bacopa monnieri* by HPLC; Phytochemical Analysis 16, pp. 24-29 )2005).
Djerassi C et al., J. Biol Chem. Jan. 1952; 194(1) 115-8.

Eisenreichova E et al ., A new steroidal saponin from the bulbs of *Lilium candidum* ., Pharmazie (2000) 55 (7) pp. 549-550.
Faul William h et al., Side-chain Transformations and Deuterium Labeling in the Steroidal Sapogenin Series., J. Org. Chem. vol. 35, No. 8, 1970 pp. 2571-2585.
Gautam et al., Immunomodulatory activity of Asparagus racemosus on systemic Thl/Th2 immunity, Implications for immuno adjuvant potential. J. ethnopharmacology, 121, 241-247 (2009).
Girardon P et al., Volatile Constituents of Fenugreek Seeds, Planta Medica 1985, pp. 533-534.
Hayes PY., et al, Structural revision of shatavarins I and IV, the major components from the roots of *Asparagus racemosus*, Tetrahedron Letters 47 (2006) 6965-6969.
Hou C et al., Bacopaside III, Bacopasaponin G, and Bacopasides A, B, and C from *Bacopa Monniera*, J. Nat. Prod 2002, 65 1759-1763.
Hu K et al., Protodioscin (NSC-698 796) Its Spectrum of Cytotoxicity Against Sixty Human Cancer Cell Lines in an Anticancer Drug Screen Panel, Planta Med 2002; 68: 297-301.
Hu K et al., The cytotoxicity of protoneodioscin (NSC-698789), a furostanol saponin from the rhizomes of *Dioscorea collettii* var. *hypoglauca*, against human cancer cells in vitro, Phytomedicine 9: 560-565, 2002.
Hu K et al., The Cytotoxicity of Methyl Protoneodioscin (NSC-698791) Against Human Cancer Cell Lines in Vitro: Anticancer Research 22: 1001-1006 (2002).
Hu K et al., Antineoplastic Agents; 1. Three Spirostanol Glycosides from Rhizomes of *Dioscorea Collettii* var. *hypoglauca*: Planta Medica 62 (1996) 573-575.
Inamdar AC et al., Comparison between Shatavar and *Asparagus* Spp.: Bioyigyanam 6: 27-35, 1980.
Inoue T et al., Steroidal Glycosides from *Allium Macleanii* and *A. Senescens*, and their inhibitory activity on tumour promoter-induced phospholipid Metabolism of Hela Cells: Phytochemistry vol. 40, No. 2, pp. 521-525 (1995).
Jin M et al., Cytotoxic Steroidal Saponins from *Polygonatum zanlanscianense*, J. Nat. Prod. , 67, 1992-1995. (2004).
Joussen AM et al., Nonsteroidal anti-inflammatory drugs prevent early diabetic retinopathy via TNF-α suppression: The FASAB Journal, Mar. 2002, vol. 16 pp. 438-440.
Kostova I et al., Two new sulfated Furostanol Saponins from *Tribulus terrestris*: Z Naturforsch, 57c, pp. 33-38 (2002).
Li M et al., Synthesis of monomethylated dioscin derivatives and their antitumor activities: Carbohydrate Research 338 (2003) 117-121.
Liu M et al., Synthesis of (25*R*)-ruscogenin-l-yl β-D-xylopyranosyl-(1→3)-[β-D-glucopyranosyl-(1→2)]-β-D-fucopyranoside: Carbohydrate Research 329 (2000) 745-754.
Liu H et al., New Furostanol Glycosides from the Rhizomes of *Dioscorea Futschauensis* R. Kunth:Journal of Asian Natural Products Research 2003, vol. 5 (4) pp. 241-247.
Liu M et al., Diosgenin induces cell cycle arrest and apoptosis in human leukemia K562 cells with the disruption of $Ca^{2+}$ homeostasis: Cancer Chemother Pharmacol (2005) 55: 79-90.
Madar Z et al., Fenugreek (*Trigonella Foenumgraecum*) as a means of reducing postprandial glucose level in diabetic rats: Nutrition Reports International Jun. 1984, vol. 29, No. 6, pp. 1267-1273.
Mahato SB et al., Bacopasaponins E and F: two jujubogenin bisdesmosides from *Bacopa monniera*: Phytochemistry 53 (2000) 711-714.
Markine-Goriaynoff N et al., The core 2 β-1, 6-*N*-acetylglucosaminyltransferase-M encoded by bovine herpesvirus 4 is not essential for virus replication despite contributing to post-translational modifications of structural proteins: Journal of General Virology (2004) 85, 355-367.
Melo PS et al., Cytotoxicity of phytosterol diosgenin and its derivatives in rat cultured hepatocytes and V79 fibroblasts: Human & Experimental Toxicology (2004) 23, 487-493.
Nakamura T et al., Interaction of Saponins with red blood cells as well as with the phosphatidylcholine liposomal membranes; J> Pharm Dyn. 2, 374-382 (1979).
Nian H et al., Protective effect of steroidal saponins from rhizome of *Anemarrhena asphodeloides* on ovarietomy-induced bone loss in rats; Acta Pharmacologica Sinica Jun. 2006: 27 (6) pp. 728 734.

(56) References Cited

OTHER PUBLICATIONS

Paseshnichenko VA et al., Isolation and Properties of Saponins from dioscorea deltoidea Rhizomes; Applied Biochem. Microbiol. 1975, II (1) p. 83-90.
Pawar R et al., Dammarane Triterpene Saponin from *Bacopa monniera* as the Superoxide inhibitor in Polymorphonuclear Cells; Planta Med 67 (2001) pp. 752-754.
Quan HJ et al., Preparations of heterospirostanols and their pharmacological activities; Eur. J Med. Chem 37 (2002) pp. 659-669.
Raju J et al., *Trigonella foenum graecum* (fenugreek) seed powder improves glucose homeostasis in alloxan diabetic rat tissues by reversing the altered glycolytic, gluconeogenic and lipogenic enzymes; Molecular and Cellular Biochemistry 224: 45-51, 2001.
Ribes G et al., Effects of Fenugreek Seeds on Endocrine Pancreatic Secretions in Dogs; Ann Nutr Metab 28: 37-43 (1984).
Shao Y et al., Anti-tumor activity of the crude saponins obtained from asparagus; Cancer Letters 104 (1996), 31-36.
Shao Y et al.,Steroidal Saponins from *Asparagus officinalis* and Their Cytotoxic Activity; Planta Medica 63 (1997) 258-262.
Sharma RD; Effect of Fenugreek Seeds and Leaves on Blood Glucose and Serum Insulin Responses in Human Subjects; Nutrition Research, vol. 6, pp. 1353-1364 (1986).
Sharma SC et al; Steroidal Saponins of *Asparagus adscendens*; Phytochemistry, vol. 21, No. 8, pp. 2075-2078 (1982).
Shimomura H et al; 26-O-Acylated Furostanol Saponins Pardarinoside A and B from the Bulbs of Lilium Pardarinum; Chem. Pharm. Bull. 36 (8) 3226-3229, 1988.
Sheilds et al Acute Multiple Sclerosis, characterized by extensive mononuclear phagocyte infiltration. Neurochem. res. 25, 1517-1520. (2000).
Singh SB et al., Furostanol Saponins from *Paris Polyphylla* Structures of Polyphyllin G and H; Phytochemistry, vol. 21, No. 8, pp. 2079-2082, 1982.
Sinha J et al; Bacopasaponin C: Critical Evaluation of Anti-Leishmanial Properties in Various Delivery Modes; Drug Delivery, 9: 55-62, 2002.
Sur P et al; *Trigonella Foenum graecum* (Fenugreek) Seed Extract as an Antineoplastic Agent; Phytotherapy Research, 15 257-259 (2001).
Spruce et al (2004) Intrinsic factors implicated in the sequence of diabetic neuropathy and foot ulceration: a potential role of core2 betal, 6-N-acetylglucoseaminyltransferase (core2GlcNAcT-I) [core 2 transferase]. Diabetic Medicine, 21 (Suppl. 2), 1-35.
Vachalkova A et al., Potential carcinogenic and inhibitory activity of compounds isolatyed from *Lilium candidum* L; Neoplasma, 47, 5, 2000 pp. 313-318.
Vasileva.,. Composition and Biological Activity of Steroidal Glycosides from cell suspensions of *Dioscorea deltoidea* Wall. Prikl Biokhim Mikrobiol 1995, vol. 31 (2) pp. 238-242. English Abstract.
Vasileva, Isolation and properties of Saponins from Dioscorea deltoidea Wall Rhizomes. Prikl Biokhim Mikrob, 1975, II (1), p. 94-101—English Abstract.
Van Der Elst I and Datti A. β1,6 N-Acetylglucosaminyltransferase (core 2 GlcNAc-T) expression in normal rat tissues and different cell lines: evidence for complex mechanisms of regulation. Glycobiology vol. 8 No. 7 pp. 731-740, (1998).
Vasileva, Composition and Biological Activity of Steroid Glycosides from Cell Suspensions of *Discorea Deltoidea* Wall; Applied Biochemistry and Microbiology, vol. 31, No. 2 1995, pp. 206-209.
Vasyukova NI., Fungitoxic Properties of Steroid Saponins from *Dioscorea deltodea* Rhizomes; Applied Biochem Microbiol. 1977, 13 (2) pp128-131.
Yu J et al., Progress in studies on chemical constituents and pharmacological effect of Trigonella foenum-graecum. Chinese traditional and Herbal Drugs, 34(12) 1146-1149 (2003).
Li C et al., Synthesis of diosgenyl α-L rhamnopyranosyl-(1→2)-[β-D-glucopyrampsyl-{1→3]-β-D-glucopyranoside {gracillin} amd related saponins;Carbohydrate Research 306 (1998) p. 189-195.
Yu B et al., First Synthesis of a Bidesmosidic Triterpene Saponin by a Highly Efficient Procedure; J.AM.Chem.Soc. 1999, 121, pp. 12196-12197.

Zou CC et al., the synthesis of gracillin and dioscin: two typical representatives of spirostanol glycosides; Carbohydrate Research 338 (2003) pp. 721-727.
Battistini, L. et al; "CD8[+] T cells from patients with acute multiple sclerosis display selective increase of adhesiveness in brain venules: a critical role for P-selectin glycoprotein ligand-1", *Blood*, vol. 101 No. 12, 4775-4780 (2003).
Ben-Mahmud, Bahaedin M, et al; "Tumor Necrosis Factor-α in Diabetic Plasma Increases the Activity of Core 2 GLcNAc-T and Adherence of Human Leukocytes to Retinal Endothelial Cells"; *Diabetes*, vol. 53, 2968-2976 (2004).
Brockhausen, I., et al; "Biosynthesis of O-Glycans in Leukocytes from Normal Donors and from Patients with Leukemia: Increase in O-Glycan Core 2 UDP-GlcNAc:Galβ1-3GalNAc-R (GlcNAc to GalNAc) β1(1-6)-N-Acetylglucosaminyltransferase in Leukemic Cells"; *Cancer Research*; 51, 1257-1263 (1991).
Buerke, Michael, et al; "Sialyl Lewis[x]—Containing Oligosaccharide Attenuates Myocardial Reperfusion Injury in Cats"; *J. Clin. Invest.*; vol. 93, 1140-1148 (1994).
Beum, P. V. and Cheng, Pi-W.; "Biosynthesis and Function of β1,6 Branched Mucin-Type Glycans"; *The Molecular Immunology of Complex Carbohydrates-2* (2001).
Beum, P. V., et al; "Mucin biosynthesis: upregulation of core 2 β1,6 N-acetylglucosaminyltransferase by retinoic acid and Th2 cytokines in a human airway epithelial cell line"; *Am. J Physiol Lung Cell Mol. Physiol.*; 288: L116-L124 (2005).
Beum, P. V., et al; "Mucin Biosynthesis Epidermal Growth Factor Downregulates Core 2 Enzymes in a Human Airway Adenocarcinoma Cell Line"; *Am. J. Respir. Cell Mol. Biol.*; vol. 29, 48-56 (2003).
Celie, J.W.A.M, et al; "Identification of L-Selectin Binding Heparan Sulfates Attached to Collagen Type XVIII"; *J. Biol Chem.*; 280(29); 26965-73; Epub (2005).
Dennis, James W.; "Glyco-Forum Section; Core 2 GlcNAc-Transferase and polylactosamine expression in O-glycans", Glycobiology; vol. 3, No. 2, pp. 91-96 (1993).
Dube, Danielle H. et al, "Glycans in Cancer and Inflammation—Potential for Therapeutics and Diagnostics", *Nature Reviews*, vol. 4, No. 6, 477-288 (2005).
Duan, L-L. et al; "Regulation of Metastasis-Suppressive Gene Nm23-H1 on Glycosy-transferases Involved in the Synthesis of Sialy Lewis Antigens"; *J. Cell. Biochem.*; 94:1248-1257 (2005).
Fox, R.I., et al; "A Novel Cell Surface Antigen (T305) Found in Increased Frequency on Acute Leukemia Cells and in Autommune Disease States"; *J. Immunol.* vol. 131, No. 2, 761-767 (1983).
Foxall, C. et al; "The Three Members of the Selectin Receptor Family Recognize a Common Carbohydrate Epitope, the Sialyl Lewisx Oligosaccharide"; *J. Cell Biol.*; vol. 117, 895-902 (1992).
Fugang P. et al.; "Post Translational Modifications of Recombinant P-selectin Glycoprotein Ligand-1 Required for Binding to P and E-selectin"; *J. Biol. Chem.*; vol. 271, No. 6, 3255-3264 (1996).
Fujita, M. et al; "Pulmonary hypertension in TNF-α-overexpressing mice is associated with decreased VEGF gene expression"; *J. Applied Physiol*; vol. 93, 2162-2170 (2002).
Goss, P. E. et al; "Inhibitors of Carbohydrate Processing: A New Class of Anticancer Agents[1,2]"; *Clin. Cancer Res.*; vol. 1, 935-944 (1995).
Maaheimo,Hannu et al, "Synthesis of a divalent sialyl Lewis x O-glycan, a potent inhibitor of lymphocyte-endothelium adhesion"; *Eur J. Biochem*; 234, 616-625 (1995).
Hiraoka, N. et al; "Core 2 Branching β1,6-N-Acetylglucosaminyltransferase and High Endothelial Venule-restricted Sulfotransferase Collaboratively Control Lymphocyte Homing"; *J Biol Chem.*; vol. 279, No. 4, 3058-3067 (2004).
Kumar, A. et al; "Recombinant Soluble Form of PSGL-1 Accelerates Thrombolysis and Prevents reocclusion in a Porcine Model"; *Circulation*; 99, 1363-1369 (1999).
Jain, Rakesh K et al, "Inhibition of L-and P-selectin by a rationally synthesized novel core 2-like branched structure containing GalNAc-Lewis[x] and Neu5Acα2-3Galβ1-3GalNAc sequences"; *Glycobiology*, vol. 8, No. 7; 707-717 (1998).
Jones, Steven P.; "A Bittersweet Modification O-GlcNAc and Cardiac Dysfunction"; *Circ Res.*; 96; 925-926 (2005).

(56) References Cited

OTHER PUBLICATIONS

Kamisako, Toshinori et al, "Regulation of biliary cholesterol secretion is associated with abcg5 and abcg8 expressions in the rats: effects of diosgenin and ethinyl estradiol", *Hepatology Research* 26; 348-352 (2003).

Lewis, M.J. and D 'Cruz D.; "Adhesion molecules, mycophenolate mofetil and systemic lupus erythematosus"; *Lupus*, 14, 17-26 (2005).

Martininez, M. et al; "Regulation of PSGL-1 Interactions with L-selectin, P-selectin, and E-selectin"; *J. Biol. Chem.*, vol. 280, No. 7, 5378-5390 (2005).

Merzaban, Jasmeen S. et al.; "An Alternate Core 2 β,6-$N$-Acetylglucosaminyltransferase Selectively Contributes to P-Selectin Ligand Formation in Activated CD8 T Cells1"; *The Journal of Immunology*, 174: 4051-4059 (2005).

Morin, M.J. and Bernacki, R.J.; "Biochemical Effects and Therapeutic Potential of Tunicamycin in Murine L1210 Leukemia"; *Cancer Res.* 43, 1669-1674 (1983).

Nakamura, M. et al.; "Single Glycosyltransferase, Core 2β1-6-$N$-acetylglucosaminyltransferase, Regulates Cell Surface Sialy-Le$^x$ Expression Level in Human Pre-B Lymphocytic Leukemia Cell Line KM3 Treated with Phorbolester"; *J Biol. Chem.*; 273, No. 41; 26779-26789 (1998).

Narumi, S. et al; "Tissue-Specific Induction of E-Selectin in Glomeruli is Augmented following Diabetes mellitus"; *Nephron*; 89, 161-171 (2000).

Okada, S. et al; "Intercellular Adhesion Molecule-l-Deficient Mice are Resistant Against Renal Injury After Induction of Diabetes"; *Diabetes*; 52:2586-2593 (2003).

Piccio L. et al; "Molecular Mechanisms Involved in Lymphocyte Recruitment in Inflamed Brain Microvessels: Critical Roles for P-Selectin Glycoprotein Ligand-1 and Heterotrimeric G$_i$-Linked Receptors1"; *J. Immunol.*; 168: 1940-1949 (2002).

Ravnskov, U; "Is atherosclerosis caused by high cholesterol?", *Q J Med*; 95, 397-403 (2002).

Ross, Russell; "Atherosclerosis—An Inflammatory Disease", *The New England Journal of Medicine*, vol. 340, 2, 115-126 (1999).

Simmons, Rex D. and Brenda A. Cattle; "Sialyl Ligands facilitate lymphocyte accumulation during inflammation of the central nervous system", *Journal of Neuroimmunology*, 41; 123-130 (1992).

Steinberg, D.; "Atherogenesis in perspective: Hypercholesterolemia and inflammation as partners in crime"; *Nature Medicine*; vol. 8, No. 11; 1211-1217 (2002).

Steinman, Lawrence; "Blocking Adhesion Molecules as Therapy for Multiple Sclerosis: Natalizumab"; *Nature Reviews: Drug Discovery*, vol. 4, 510-518 (2005).

Baek, Suk Hwan, et al, "Inactivation of Human Pleural Fluid Phospholipase A$_2$ by Dioscin"; *Arch. Pharm. Res.*; vol. 17, No. 4, 218-222 (1994).

Ulbrich, Holger, et al; "Leukocyte and endothelial cell adhesion molecules as targets for therapeutic interventions in inflammatory disease"; *Trends in Pharmacological Sciences*, vol. 24, No. 12; 640-647 (2003).

Williams, D. et al; "Mucin Synthesis II. Substrate Specificity and Product Identification Studies on Canine Submaxillary Gland UDP-GlcNAc:Galβ1-3GalNAc(GlcNAc—GalNAc) β6-$N$-acetylglucosaminyltransferase"; *J. Biol. Chem.*; 255, No. 23; 1253-1261 (1980).

Yanagihara, K, et al; "Lipopolysaccharide Induces Mucus Cell Metaplasia in Mouse Lung"; *Am. J. Respir. Cell Mol. Biol.*; 24, 66-73 (2001).

Zak, I., et al; "Selectin Glycoprotein Ligands"; *Acta Biochemica Polonica*; vol. 47, No. 2; 393-412 (2000).

\* cited by examiner

Figure 2: The structures of Gracillin and Protogracillin.
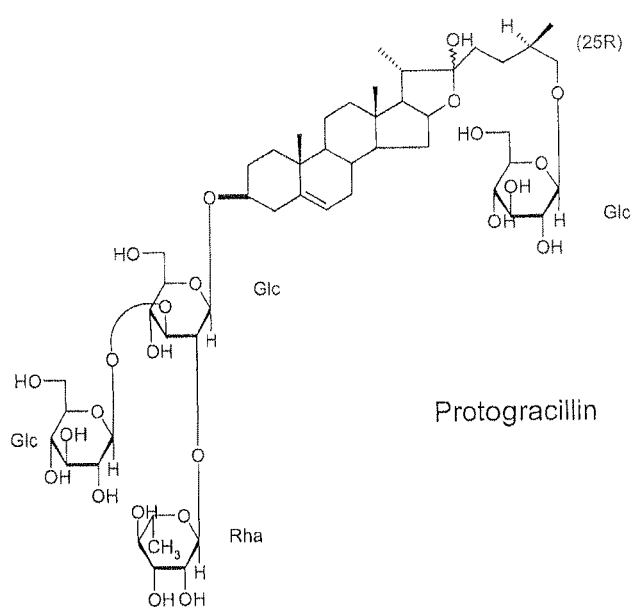
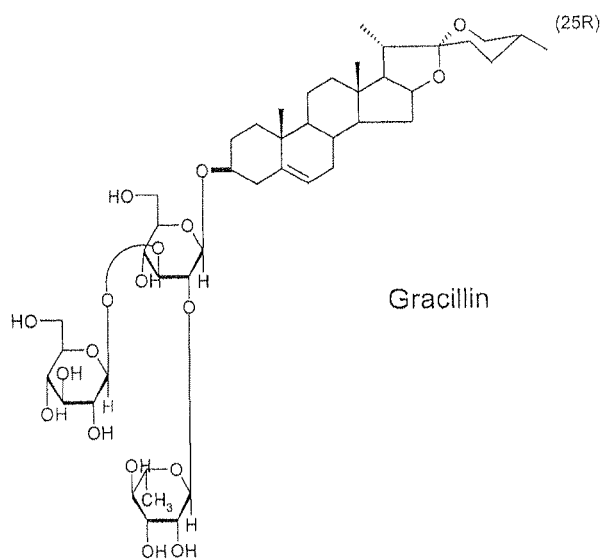

CORE 2 GLCNAC-T INHIBITORS

This application is a continuation of application Ser. No. 11/481,255 filed Jul. 6, 2006 now abandoned which claims priority to British Application No. 0513888.8 filed Jul. 6, 2005, the entire contents of each of which are hereby incorporated by reference.

The present invention relates to the use of known and novel compounds as pharmaceutical actives against diseases susceptible to treatment by modulation, eg. inhibition, of the enzyme Core 2 GlcNAc-transferase (EC 2.4.1.102), also known as UDP-GlcNAc:Galβ1,3GalNAc—R (GlcNAc to GalNAc) β-1,6-N-acetylglucosaminyl transferase (core 2 β-1,6 N-acetylaminotransferase, hereinafter referred to as Core 2 GlcNAc-T.

Inhibitors of Core 2 GlcNAc-T, and the present compounds in particular, have application in therapy for diseases in which core 2 GlcNAc-T is implicated and especially those in which the enzyme activity is raised relative to the normal level in the tissue type concerned, or those conditions in which it is advantageous to lower the activity of core 2 GlcNAc-T for example to its normal level or below. Examples of such conditions are inflammatory diseases such as atherosclerosis and multiple sclerosis, diabetes, cancer and its metastasis.

Inhibitors of Core 2 GlcNAc-T are known but none are n clinical development as isolated actives for pharmaceutical use. Examples of known compounds are disclosed in. WO0187548, Kuhns (17), Hindsgaul (37) and Toki (38).

Applicant's co-pending application PCT/GB2004/005398 (incorporated herein by reference) discloses known and novel steroidal glycosides that have therapeutic use as Core GlcNAc-T inhibitors, discusses the basis for use of such inhibitors in therapy and discloses published documents detailing the basis for Core 2 GlcNAc-T involvement in a number of diseases. The present application discloses further steroidal glycoside compounds that are inhibitors of core 2 GlcNAc-T and additional conditions in which these compounds have a therapeutic use.

Some of the presently disclosed steroidal glycosides have been tested previously in a limited number of disease paradigms. For example in protection against gastric mucosal lesions in rats (JP2004-143126 and 78), in mouse ear edema tests for anti inflammatory activity (81), in the prevention of senility (WO9916786) and as adjuvants (82). CN1243129 and CN1237583 disclose the use of certain compounds presently disclosed in cancer and some compounds have been used in in vitro cytotoxicity assays (e.g. 39, 42, 46, 55, 56, 59, 79, 80), however the levels of activity in cell based assays are far below those currently disclosed for inhibition of Core 2 GlcNAc-T activity. None of the aforementioned publications discloses that certain steroidal glycosides are inhibitors of Core 2 GlcNAc-T.

Certain plant sterol compounds, used as dietary supplements, impede the uptake of cholesterol from the gut and consequently lower plasma LDL cholesterol. However these compounds are generally used in doses of several grams per day and are not known to be inhibitors of Core 2 GlcNAc-T.

In a first aspect the present invention is provided a method of treating a subject in need of therapy for a condition involving detrimental activity of the enzyme core 2 GlcNAc-T, particularly raised activity, comprising administration of a therapeutically effective amount of an inhibitor of core 2 GlcNAc-T of formula I to a patient in need thereof

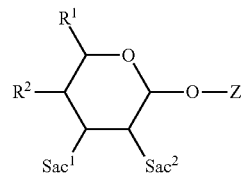

wherein:
$R^1$ is H, $C_{1-6}$ alkyl, $C_{1-6}$ hydroxyalkyl, $C_{1-6}$ alkoxy or $C_{1-6}$-alkoxy-$C_{1-6}$-alkyl;
$R^2$ is H, —OH or $C_{1-6}$ alkoxy;
$Sac^1$ and $Sac^2$ are independently selected saccharide moieties; and
Z is a steroid moiety attached to the oxygen shown by its 3 position ring carbon
or a pharmaceutically acceptable salt, ether, ester or tautomer thereof.

The ring of formula I is designated ring A.

The prior art associates Core 2 GlcNAc-T (particularly through its involvement with branched oligosaccharide synthesis) with inter alia, vascular diseases, (including complications of diabetes), autoimmune and inflammatory conditions. Particular conditions subject to treatment by the present invention are myopathy, retinopathy, nephropathy, atherosclerosis, asthma, rheumatoid arthritis, inflammatory bowel disease, transplant rejection, ischemia reperfusion injury (e.g. stroke, myocardial ischemia, intestinal reperfusion eg after hemorrhagic shock,), restenosis, ileitis, Crohn's disease, thrombosis, cholitis including for example ulcerative cholitis), lupus, frost bite injury, acute leukocyte mediated lung injury (e.g. adult respiratory distress syndrome), traumatic shock, septic shock, nephritis, psoriasis, cholicytitis, cirrhosis, diverticulitis, fulminant hepatitis, gastritis, gastric and duodenal ulcers, hepatorenal syndrome, irritable bowel syndrome, jaundice, pancreatitis, ulcerative cholitis, human granulocyte ehlichiosis, Wiskott-Aldrich syndrome T-cell activation, AIDS, infection with viruses, bacteria, protozoa and parasites adapted to use particular core 2 derived glycans and cancer. Cancer metastasis is a particularly treatable by the present method,(see references 1-16, 67-77 and 83-87, incorporated herein by reference).

Cancers include leukemias, lymphomas, melanomas, adenomas, sarcomas, and carcinomas of solid tissues; particularly cancers include prostate, testicular, mammary, pancreatic, cervical, uterine, kidney, lung, rectum, breast, gastric, thyroid, neck, cervix, bowel, salivary gland, bile duct, pelvis, mediastinum, urethra, bronchogenic, bladder, esophagus, colon, small intestine and sarcomas (e.g. Kaposi's sarcoma) and adenomatous polyps. Particularly susceptible cancers for treatment are oral cavity carcinomas, pulmonary cancers such as pulmonary adenocarcinoma, colorectal cancer, bladder carcinoma, liver tumours, stomach tumours colon tumours, prostate cancer, testicular tumour, mammary cancer, lung turnouts oral cavity carcinomas.

Particular application is found in cancer or its metastasis where Core 2 GlcNAc-T activity is raised.

Compound of the formula Iare compounds wherein
$R^1$ is H, $C_{1-6}$ alkyl, $C_{1-6}$ hydroxyalkyl, $C_{1-6}$ alkoxy or $C_{1-6}$-alkoxy-$C_{1-6}$-alkyl; preferably $R^1$ is H, $C_{1-6}$ alkyl or $C_{1-6}$ hydroxyalkyl more preferably $R^1$ is —H, —CH$_3$ or —CH$_2$OH; more preferably still $R^1$ is —CH$_2$OH; more preferably still $R^1$ is —CH$_2$OH and ring A is a glucose or galactose moiety; most preferably glucose.

$R^2$ is H, —OH or $C_{1-6}$ alkoxy; preferably $R^2$ is H or —OH;

$Sac^1$ and $Sac^2$ are independently selected saccharide moieties; and

Z is a steroid moiety attached to the oxygen shown by its 3 position ring carbon or a pharmaceutically acceptable salt, ether, ester or tautomer thereof.

Saccharides $Sac^1$ and $Sac^2$ include, but are not limited to, monosaccharides, disaccharides, trisaccharides, tetrasaccharides and polysaccharides. Preferably $Sac^1$ and $Sac^2$ are monosaccharides, but may be independently selected as di- or oligosaccharides.

Preferably $Sac^1$ and $Sac^2$ are independently selected from a tetrose a pentose and a hexose;

Preferably $Sac^1$ is selected from a pentose, a deoxy aldohexose and an aldohexose; more preferably $Sac^1$ is selected from arabinose, xylose, quinovose rhamnose or an aldohexose, more preferably $Sac^1$ is selected from the group consisting of arabinose, xylose, quinovose, rhamnose, glucose, mannose, gulose, altrose, allose idose and talose, more preferably still $Sac^1$ is rhamnose or glucose; most preferably it is glucose.

Preferably $Sac^2$ is selected from a pentose, a deoxy-aldohexose and an aldohexose; more preferably $Sac^2$ is selected from arabinose, xylose, glucose, mannose, galactose, and a deoxyaldohexose; more preferably $Sac^2$ is selected from the group consisting of arabinose, xylose, glucose, mannose, galactose, and a 6-deoxyaldohexose; more preferably $Sac^2$ is selected from. glucose, galactose, arabinose, xylose and rhamnose; more preferably it is rhamnose.

In a preferred combination the group A is glucose or galactose, $Sac^1$ arabinose, xylose, quinovose, rhamnose, glucose, mannose, galactose, altrose, allose idose and talose, more preferably is glucose or rhamnose and $Sac^2$ is rhamnose Particularly preferred are compounds of the formula III

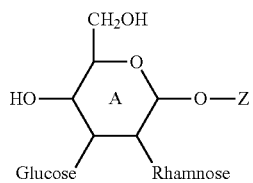

Wherein the ring A is a glucose moiety, and which formula may be written:

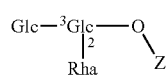

most preferred are compounds which are 6-deoxy-α-L-mannopyranosyl (1→2)-O-[β-D-glucopyranosyl-(1→3)]-β-D-glucopyranosides of steroid moiety Z.

Wherein Glc is glucose and Rha is rhamnose and 2 and 3 refer to the position of attachment to the central Glc group.

The term "steroid moiety" denotes a moiety comprising a tetracyclic ring system shown as formula V:

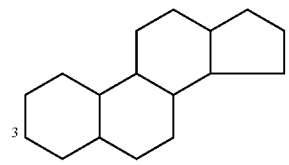

Typically the saccharide ring, A, is attached to the steroid moiety Z at the 3 position.

Typically the steroid moiety ring system is modified, for example by the addition of one or more further rings and/or one or more double bonds and/or one or more substituents.

The steroid moiety may for example have the ring system of cholestane, pregnane, androstane, estrane, cholesterol, cholane, progestin, a mineralocorticoid, such as dehydroepiandrosterone or its 7-keto or 7-hydroxy analogue or a bile acid.

In one preferred embodiment the steroid moiety is that of a steroid that is in itself beneficial or neutral. By neutral is meant that the steroid ring is that which is considered suitable, whether as approved e,g, by the FDA or as GRAS, for use in a human or animal. By beneficial is meant that the steroid has effects of benefit to the human or animal if it were administered separately.

The steroid moiety Z may for example be that of a steroidal sapogenin derivable from a natural source (for example a plant source) or a steroidal moiety which is itself derivable from such plant steroidal sapogenins by chemical modification. The sapogenin may for example be that of a furostanol glycoside, a spirostanol glycoside (including those with nitrogen and oxygen containing rings) a damarane glycoside or other steroidal saponin.

The steroid moiety Z for example may be a steroid moiety of the formula VI

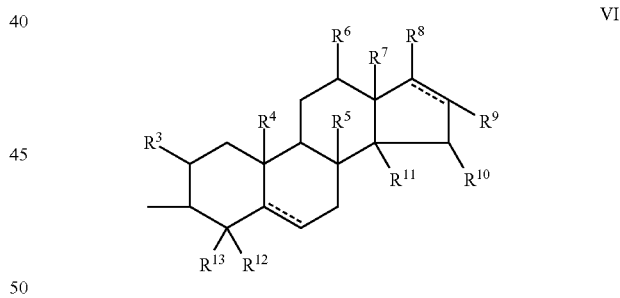

Groups or rings that may be incorporated into the steroid core V or VI are selected from those set out in formulae VI a to VI e wherein the dotted lines represent the relevant rings of the steroid core,

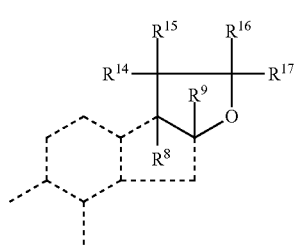

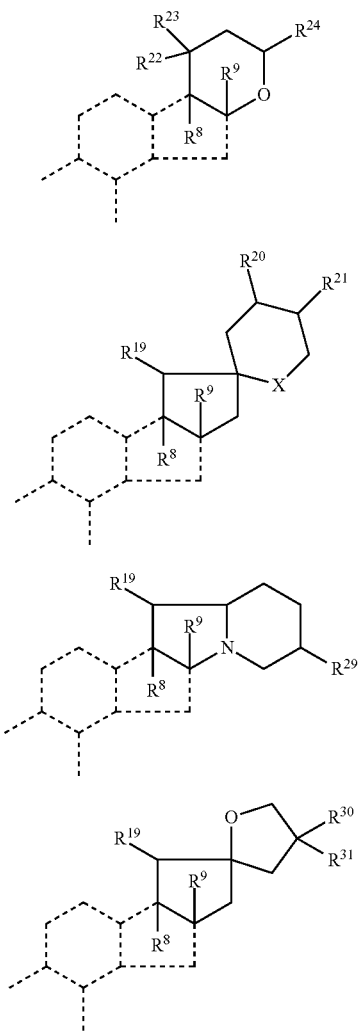

VIb

VIc

VId

VIe wherein:

$R^3$, $R^{10}$, $R^{18}$ and $R^{20}$ are independently selected from H and —OH;

$R^4$ $R^{14}$, $R^{19}$, $R^{23}$ $R^{25}$ and $R^{29}$ are independently selected from $C_{1-6}$ alkyl; preferably $R^4$ $R^{14}$, $R^{19}$, $R^{23}$, $R^{25}$ and $R^{29}$ are —$CH_3$;

$R^5$, $R^7$ and $R^{12}$ are independently selected from H and $C_{1-6}$ alkyl; preferably $R^5$, $R^7$ and $R^{12}$ are independently selected from H and —$CH_3$;

$R^6$ is H or —OH or the H normally also present is absent and $R^6$ is =O;

$R^8$ is H, —OH or $C_{1-6}$ acyl or a group selected from VII a or VII b; preferably $R^8$ is H, —OH or acetyl or a group selected from VII a or VII b;

VIIa

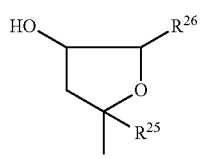

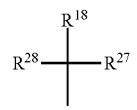

VIIb $R^9$ is H.

$R^{11}$ is H, $C_{1-6}$ alkyl or —OH or $R^9$ and $R^{11}$ taken together form a —$CH_2$—$CH_2$— group; preferably $R^{11}$ is H, —OH or —$CH_3$ or $R^9$ and $R^{11}$ taken together form a —$CH_2$—$CH_2$— group;

$R^{13}$ is H, $C_{1-6}$ alkyl or $C_{1-6}$ hydroxyalkyl; preferably $R^{13}$ is H, —$CH_2OH$, or —$CH_3$.

$R^{15}$ is H or —OH.

$R^{16}$ is H, —OH or $C_{1-6}$ alkoxy or $R^{15}$ and $R^{16}$ taken together represent the second bond of a double bond joining adjacent carbon atoms; preferably $R^{16}$ is H, —OH or —$OCH_3$ or $R^{15}$ and $R^{16}$ taken together represent the second bond of a double bond joining adjacent carbon atoms;

$R^{17}$ is $C_{1-6}$ alkyl, $C_{2-6}$ alkenyl, alkynyl, or a $C_{1-6}$ alkyl group substituted by one or more groups selected from the group consisting of —OH, $C_{1-6}$ alkoxy and $Sac^3$; preferably $R^{17}$ is $C_{2-6}$ alkenyl, or a $C_{1-6}$ alkyl group substituted by one or more groups selected from the group consisting of —OH, $C_{1-6}$ alkoxy and $Sac^3$; more preferably $R^{17}$ is $C_{2-6}$ alkenyl or a $C_{1-6}$ alkyl group substituted by one or more groups selected from the group consisting of —OH, —$OCH_3$ and $Sac^3$; more preferably still $R^{17}$ is selected from the group comprising 3-methyl but-2-enyl, 2-methyl-prop-2-enyl, 3-methylbutanyl substituted at the 4-position by $Sac^3$, 1-hydroxy-3-methylbutanyl substituted at the 4-position by $Sac^3$ or 1-methoxy-3-methylbutanyl substituted at the 4-position by $Sac^3$;

$R^{21}$ is $C_{1-6}$ alkyl, $C_{1-6}$ hydroxyalkyl or =$CH_2$; preferably $R^{21}$ is —$CH_3$, —$CH_2OH$ or =$CH_2$;

$R^{22}$ is —OH;

$R^{24}$ is $C_{1-6}$ alkyl, $C_{2-6}$ alkenyl or $C_{2-6}$ alkynyl; preferably $R^{24}$ is $C_{2-6}$ alkenyl; most preferably it is 2-methylprop-2-enyl $R^{26}$ is $C_{1-6}$ hydroxyalkyl;

$R^{27}$ is $C_{1-6}$ alkyl, $C_{1-6}$ hydroxyalkyl or $C_{1-6}$ alkyl substituted by $Sac^4$; preferably $R^{27}$ is $C_{1-6}$ alkyl or $C_{1-6}$ alkyl substituted by $S^4$; more preferably $R^{27}$ is —$CH_3$ or —$CH_2$-$Sac^4$.

$R^{28}$ is $C_{1-8}$ alkyl, $C_{2-8}$ alkenyl or $C_{2-8}$ alkynyl; preferably $R^{28}$ is $C_{1-8}$ alkyl or $C_{2-8}$ alkenyl; more preferably 3-ethyl-4-methyl-pentanyl or 5-methyl-hex-4-enyl;

$R^{30}$ is $C_{1-6}$ hydroxyalkyl or $C_{1-6}$ alkyl substituted by $Sac^5$; preferably $R^{30}$ is $C_{1-6}$ alkyl substituted by $Sac^5$; more preferably $R^{30}$ is —$CH_2$-$Sac^5$;

$R^{31}$ is $C_{1-6}$ alkyl; preferably $R^{31}$ is —$CH_3$; and $Sac^3$, $Sac^4$ and $Sac^5$ are independently selected saccharides; preferably $Sac^3$, $Sac^4$ and $Sac^5$ are independently selected monosaccharides; more preferably they are independently selected a hexose, a pentose or a tetrose; more preferably still they are independently selected from glucose, galactose, quinovose, fucose, arabinose and xylose, most preferably they are glucose.

⸺ Represents a bond that is either double or single; and

X is either O or NH; preferably X is O.

Preferred steroid moieties Z that do not incorporate further groups VI(a) to VI(e) are those in which $R^5$ is $C_{1-6}$ alkyl; $R^7$ is H; and $R^8$ is VII(a); preferably $R^5$ is $C_{1-6}$ alkyl; $R^7$ is H; $R^8$ is VII(a); $R^{11}$ is $C_{1-6}$ alkyl and $R^6$ is H or —OH; more preferably $R^5$ is $C_{1-6}$ alkyl; $R^7$ is H; $R^8$ is VII(a); $R^{11}$ is $C_{1-6}$ alkyl; $R^6$ is H or —OH, $R^{12}$ is $C_{1-6}$ alkyl and $R^{13}$ is $C_{1-6}$ alkyl or $C_{1-6}$ hydroxyalkyl.

Further preferred steroid moieties Z that do not incorporate further groups VI(a) to VI(e) are those in which $R^5$ is $C_{1-6}$ alkyl; $R^7$ is H; and $R^8$ is VII(b); preferably $R^5$ is $C_{1-6}$ alkyl; $R^7$ is H; $R^8$ is VII(b) and $R^{12}$, $R^{13}$ and $R^{11}$ are $C_{1-6}$ alkyl; more preferably $R^5$ is $C_{1-6}$ alkyl; $R^7$ is H; $R^8$ is VII(b) and $R^{12}$, $R^{13}$ and $R^{11}$ are $C_{1-6}$ alkyl and $R^6$ is H.

Further preferred steroid moieties Z that do not incorporate further groups VI(a) to VI(e) are those in which $R^5$ is H; $R^7$ is $C_{1-6}$ alkyl; and $R^8$ is $C_{1-6}$ acyl; preferably $R^5$ is H; $R^7$ is $C_{1-6}$ alkyl; $R^8$ is $C_{1-6}$ acyl; $R^{12}$ and $R^{13}$ are H; $R^{11}$ is H or —OH.

Further preferred steroid moieties Z that do not incorporate further groups VI(a) to VI(e) are those in which $R^5$ is H; $R^7$ is $C_{1-6}$ alkyl; and $R^8$ is VII b; preferably $R^5$ is H; $R^7$ is $C_{1-6}$ alkyl; $R^8$ is VIIb; $R^{12}$ and $R^{13}$ are H; and $R^{11}$ is H or —OH;

Preferred steroid moieties Z incorporating further groups VI(a) are those in which $R^5$ is H, $R^7$ is $C_{1-6}$ alkyl; $R^8$ is H or —OH; $R^{12}$ and $R^{13}$ are H and $R^{17}$ is $C_{2-6}$ alkenyl or a $C_{1-6}$ alkyl group substituted by one or more groups selected from the group consisting of —OH, —OCH$_3$ and Sac$^3$; preferably $R^5$ is H and $R^7$ is $C_{1-6}$ alkyl; $R^8$ is H or —OH; $R^{12}$ and $R^{13}$ are H and $R^{17}$ is selected from the group comprising 3-methyl but-2-eneyl, 2-methyl-prop-2-enyl, 3-methylbutanyl substituted at the 4-position by Sac$^3$, 1-hydroxy-3-methylbutanyl substituted at the 4-position by Sac$^3$ or 1-methoxy-3-methylbutanyl substituted at the 4-position by Sac$^3$.

Further preferred steroid moieties Z incorporating further groups VI(a) are those in which $R^5$ is $C_{1-6}$ alkyl, and $R^7$ is H and $R^{17}$ is $C_{2-6}$ alkenyl; preferably $R^5$ is $C_{1-6}$ alkyl, $R^7$ is H, $R^{17}$ is $C_{2-6}$ alkenyl, $R^{12}$ and $R^{13}$ are $C_{1-6}$ alkyl; more preferably $R^5$ is $C_{1-6}$ alkyl, and $R^7$ is $R^{17}$ is $C_{2-6}$ alkenyl, $R^{12}$ and $R^{13}$ are $C_{1-6}$ alkyl; more preferably $R^5$ is $C_{1-6}$ alkyl, and $R^7$ is H, $R^{17}$ is $C_{2-6}$ alkenyl, $R^{12}$ and $R^{13}$ are $C_{1-6}$ alkyl; and $R^{15}$ is —OH.

Preferred steroid moieties Z incorporating further groups VI(c) are those in which $R^5$ is H, $R^7$ is $C_{1-6}$ alkyl, $R^8$ is H or —OH, $R^{11}$ is H or —OH; $R^{12}$ and $R^{13}$ are H.

Preferred steroid moieties of formula VI (a) and VI (b) are those having the ring structures below: still more preferably having the substitutions as set forth therein.

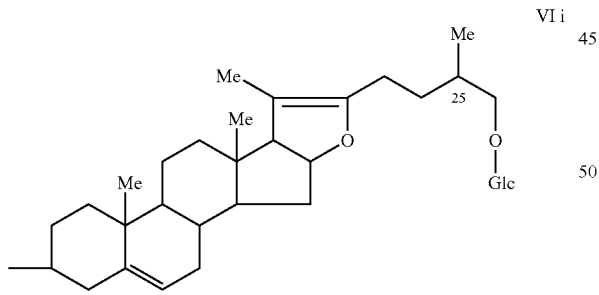

VI i

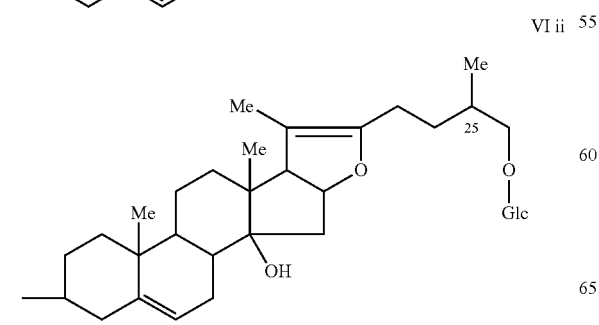

VI ii

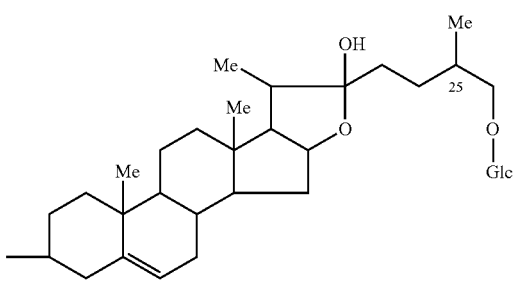

VI iii

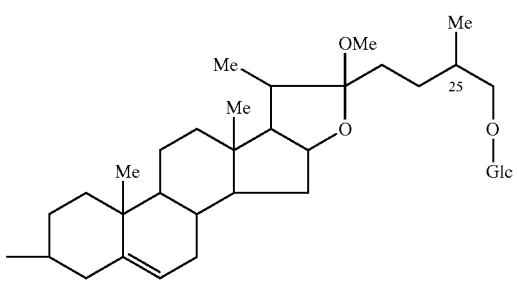

VI iv

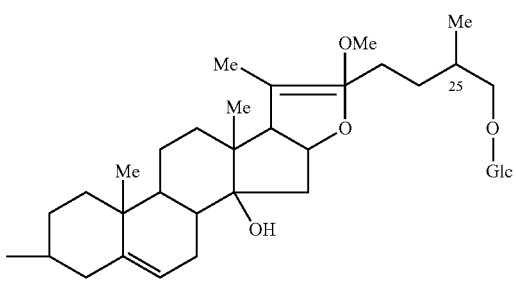

VI v

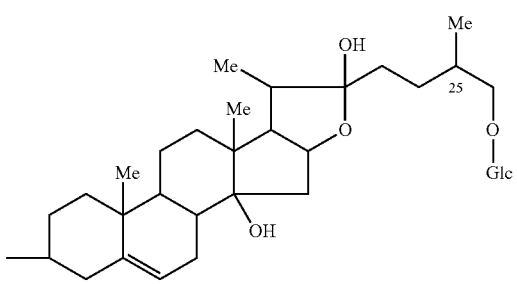

VI vi

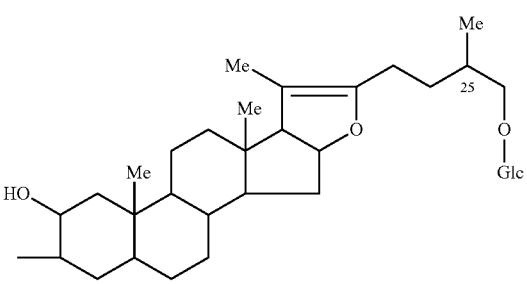

VI vii

VI viii

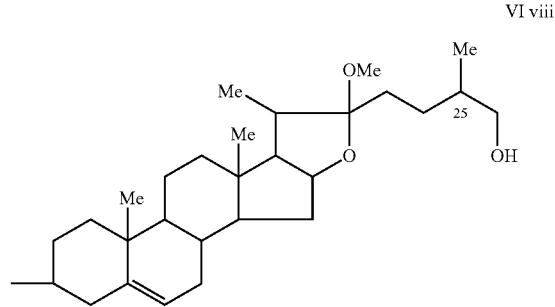

VI ix

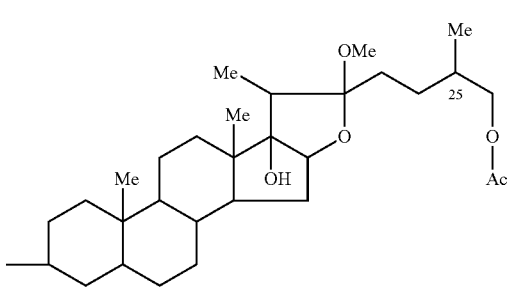

VI x

VI xi

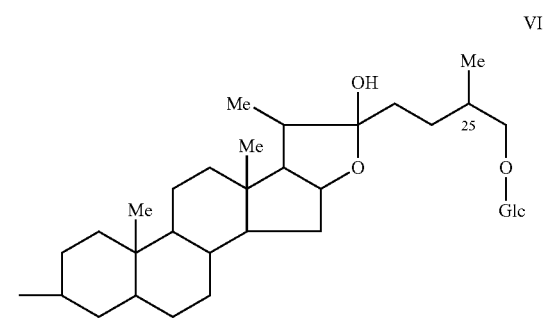

VI xii

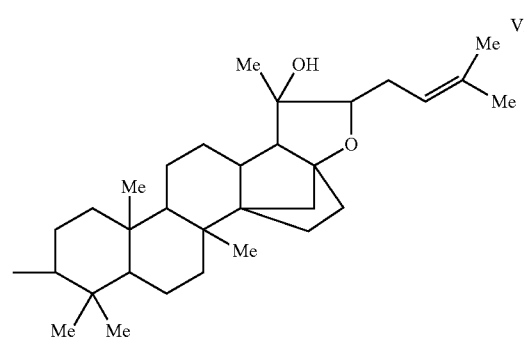

VI xiii

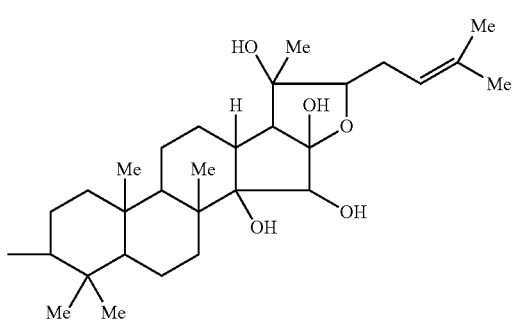

VI xiv

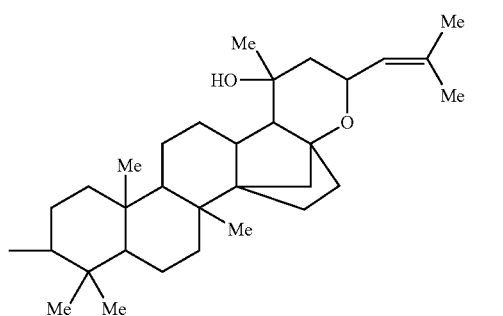

In each case the carbon atom labelled "25" can be in either the R or S configuration.

Preferred steroid moieties, Z, of the formula VI c in which X=O are for example those having the radicals of sarsasapogenin, srnilagenin, 12β-hydroxysmilagenin, rhodeasapogenin, isorhodiasapogenin, samogenin, 12β-hydroxysamogenin, markogenin, yonogenin, convallagenin A, convallagenin B, tokorogenin, tigogenin, neotigogenin, gitogenin, agigenin digitogenin, chlorogenin, paniculogenin, (25R)-spirostan-3β, 17α,21-triol, allogenin, (25R)-5α-spirostan-2α,3β,5α,6α-tetraol, (24S,25R)-5α-spirostan-2α, 3β,5α,6β,24-pentaol, yamogenin diosgenin, yuccagenin, lilagenin, ruscogenin, (25S)-ruscogenin, neopraserigenin, pennogenin, isonuatigenin, cepagenin, 24a-hydroxypennogenin, ophiogenin, sibiricogenin, convallamarogenin, neoruscogenin, hecogenin, neohecogenin, manogenin, sisalagenin and hispigenin.

Preferred steroid moieties, Z, of the formula VI c in which X=NH are for example those that have the radicals of: solasodine, soladulcidine, tomatidine and 5-dehydrotomatidine.

Preferred steroid moieties Z of the formula VI c are those having the ring structures below; still more preferably having the substitutions as set forth therein.

VI xv

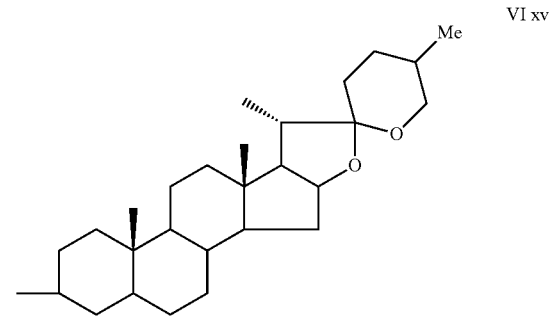

VI xvi
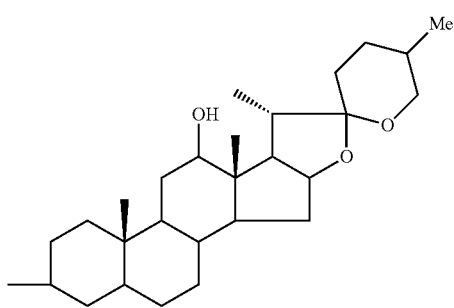
V xvii
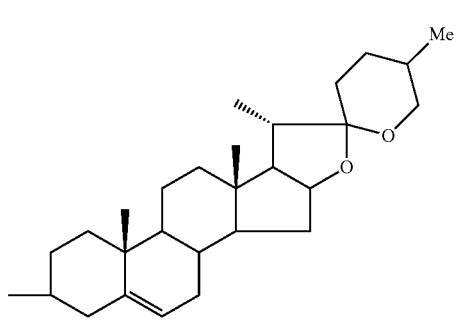
V xviii
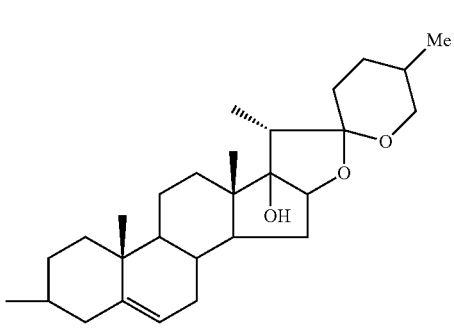
V xix
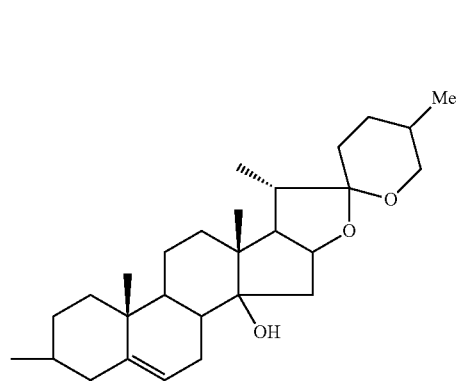
V xx
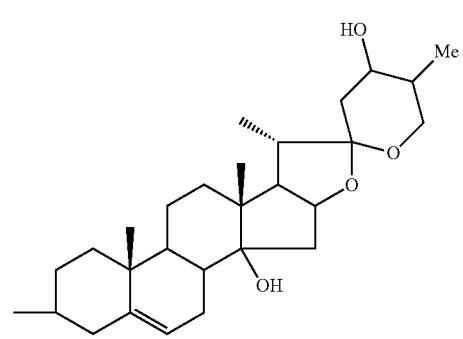
VI xxi
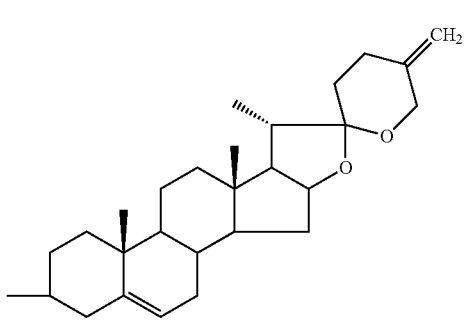
VI xxii
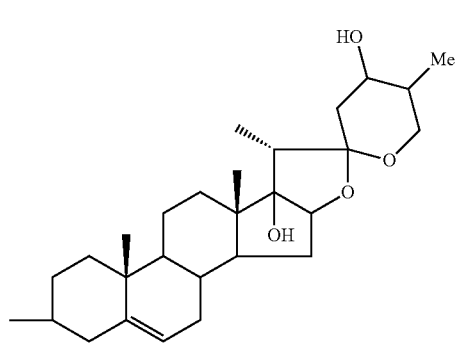
VI xxiii
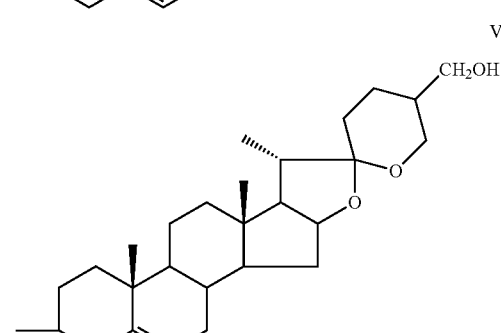
VI xxiv
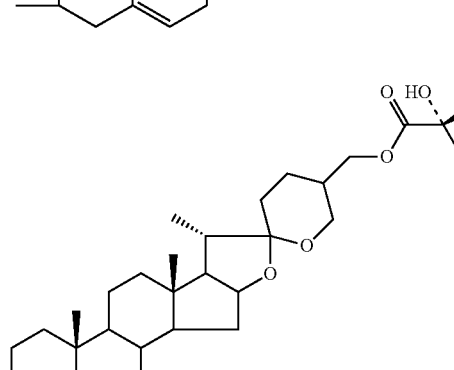
VI xxv
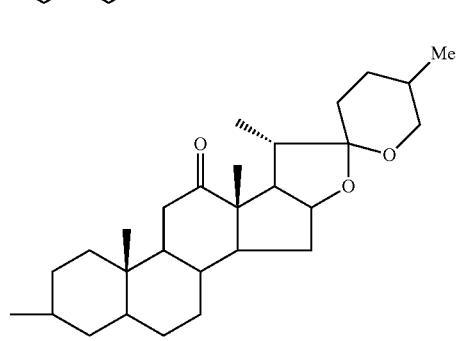

-continued

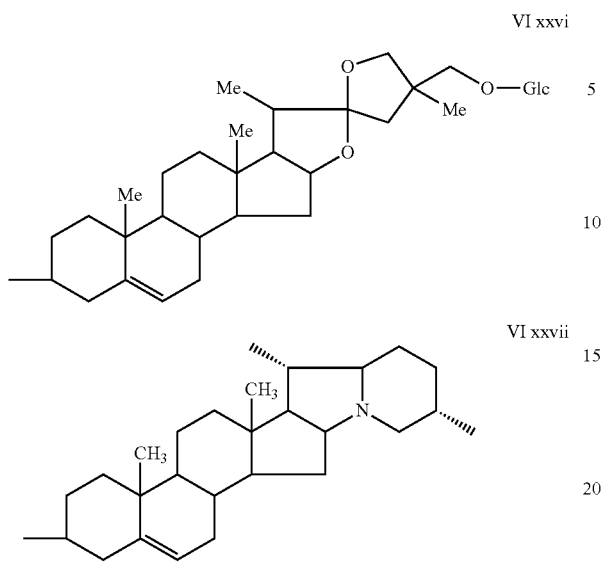

VI xxvi

VI xxvii

Further preferred steroid moieties Z of the formula VI are those having the ring structures below; still more preferably having the substitutions as set forth therein.

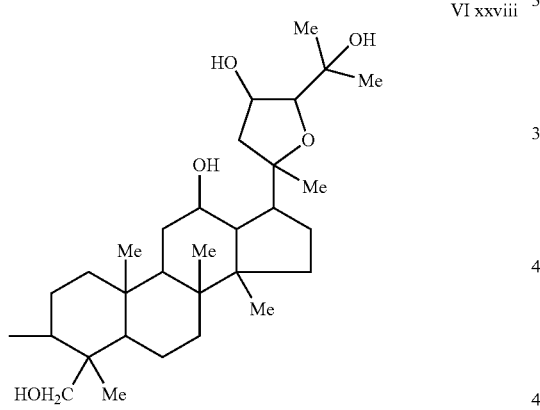

VI xxviii

VI xxix

-continued

VI xxx

VI xxxi

VI xxxii

Preferred steroid moieties VI i to VI xxxii can be derived from steroidal glycoside compounds herein or references of table 2 and further from references 19, 90 and 91).

Preferred compounds of the formula I combine any of the preferred Steroid moieties —Z— with preferred saccharide moieties.

Preferred compounds of the formula I are protogracillin proto neogracillin methylprotogracillin, methylprotoneogracillin, pseudoprotogracillin, dracenoside Q dioscoreside E , dracenoside P tuberoside C icogenin gracillin, collettiside IV 17-OH gracillin dracaenoside H dracaenoside L, dracaenoside I, lilioglycoside H, lilioglycoside I, dracaenoside D, neoalsoside A, neoalsoside C and hoduloside V, Lotoside II Further preferred compounds that are as yet un-named are compounds 17, 21 and 25 of table 2.

The preferred compounds have the following chemical names. Protogracillin is [(3β,22α,25R)-26-(β-D-glucopyranosyloxy)-22-hydroxyfurost-5-en-3-yl O-6-deoxy-α-L-mannopyranosyl (1→2)-O-[β-D-glucopyranosyl-(1→3)]-β-D-glucopyranoside], proto neogracillin is [(3β,22α,25S)-26-(β-D-glucopyranosyloxy)-22-hydroxyfurost-5-en-3-yl O-6-deoxy-α-L-mannopyranosyl (1→2)-O-[β-D-glucopyranosyl-(1→3)]-β-D-Glucopyranoside], methylprotogracillin is [(3β,22α,25R)-26-(β-D-glucopyranosyloxy)-22-methoxyfurost-5-en-3-yl O-6-deoxy-α-L-mannopyranosyl (1→2)-O-[β-D-glucopyranosyl-(1→3)]-β-D-Glucopyranoside], methylprotoneogracillin is [(3β,22α,25S)-26-(β-D-glucopyranosyloxy)-22-methoxyfurost-5-en-3-yl O-6-deoxy-α-L-mannopyranosyl (1→2)-O-[β-D-glucopyranosyl-(1→3)]-β-D-Glucopyranoside], pseudoprotogracillin is [(3β,25R)-26-(β-D-glucopyranosyloxy)furosta-5,20(22)-dien-3-yl O-6-deoxy-α-L-mannopyranosyl-(1→2)-O-[β-D-glucopyranosyl-(1→3)]-β-D-Glucopyranoside], draeenoside Q is [(3β)-26-(β-D-glucopyranosyloxy)-14-hydroxyfurosta-5,20(22)-dien-3-yl O-6-deoxy-α-L-mannopyranosyl-(1→2)-O-[β-D-glucopyranosyl-(1→3)]-β-D-glucopyranoside], dioscoreside E is [26-O-β-D-glucopyranosyl-3β,26-dihydroxy-23(S)-methoxyl-25(R)-furosta-5,20(22)-dien-3-O-α-L-rhamnopyranosyl(1→2)-[β-D-glucopyranosyl(1→3)]-β-D-glucopyranoside], dracenoside P is [(3β)-26-(β-D-glucopyranosyloxy)-14,22-dihydroxyfurost-5-en-3-yl O-6-deoxy-α-L-mannopyranosyl-(1→2)-β-D-O-[β-D-glucopyranosyl-(1→3)]-glucopyranoside, tuberoside C is [(2α,3β,5α,25S)-26-(β-D-glucopyranosyloxy)-2-hydroxyfurost-20(22)-en-3-yl O-6-deoxy-α-L-mannopyranosyl-(1→2)-O-[β-D-glucopyranosyl-(1→3)]-β-D-glucopyranoside], icogenin is [(3β,22α,25R)-26-hydroxy-22-methoxyfurost-5-en-3-yl O-6-deoxy-α-L-mannopyranosyl-(1→2)-O-[β-D-glucopyranosyl-(1→3)]-β-D-glucopyranoside], gracillin is [(3β,25R)-spirost-5-en-3-yl O-6-deoxy-α-L-mannopyranosyl-(1→2)-O-[β-D-glucopyranosyl-(1→3)]-β-D-glucopyranoside, collettiside IV is [[(3β,25S)-spirost-5-en-3-yl O-6-deoxy-α-L-mannopyranosyl-(1→2)-O-[β-D-glucopyranosyl-(1→3)]-β-D-glucopyranoside], 17-OH gracillin is [(3β,25R)-17-hydroxyspirost-5-en-3-yl O-6-deoxy-α-L-mannopyranosyl-(1→2)-O-[β-D-glucopyranosyl-(1→3)]-β-D-glucopyranoside], dracaenoside H is [(3β)-14-hydroxyspirost-5-en-3-yl O-6-deoxy-α-L-mannopyranosyl-(1→2)-O-[β-D-glucopyranosyl-(1→3)]-β-D-glucopyranoside, dracaenoside L is [(3β,24S,25R)-14,24-dihydroxyspirost-5-en-3-yl O-6-deoxy-α-L-mannopyranosyl-(1→2)-O-[β-D-glucopyranosyl-(1→3)]-β-D-glucopyranoside], dracaenoside I is [(3β)-spirosta-5,25 (27)-dien-3-yl O-6-deoxy-α-L-mannopyranosyl-(1→2)-O-[β-D-glucopyranosyl-(1→3)]-β-D-glucopyranoside], lilioglycoside H is [(3β,25S)-27-hydroxyspirost-5-en-3-yl O-6-deoxy-α-L-mannopyranosyl-(1→2)-O-[β-D-glucopyranosyl-(1→3)]-β-D-glucopyranoside], lilioglycoside I is [(3β,25R)-27-[(3S)-4-carboxy-3-hydroxy-3-methyl-1-oxobutoxy]spirost-5-en-3-yl O-6-deoxy-α-L-mannopyranosyl-(1→2)-O-[β-D-glucopyranosyl-(1→3)]-β-D-glucopyranoside], dracaenoside D is [3-[(O-6-deoxy-α-L-mannopyranosyl-(1→2)-O-[β-D-glucopyranosyl-(1→3)]-β-D-glucopyranosyl)oxy]-14-hydroxy-pregna-5,16-dien-20-one, neoalsoside A is [(3β,12β,23S,24S)-20,24-epoxy-12,23,25-trihydroxydammaran-3-yl O-6-deoxy-α-L-mannopyranosyl-(1→2)-O-[β-D-glucopyranosyl-(1→3)]-β-D-glucopyranoside], neoalsoside C is [(3β,4α,-12β,23S,24S)-20,24-epoxy-12,23,25,28-tetrahydroxydammaran-3-yl O-6-deoxy-α-L-mannopyranosyl-(1→2)-O-[β-D-glucopyranosyl-(1→3)]-β-D-glucopyranoside], hoduloside V is [(3β,16β,23R)-16,23:16,30-diepoxy-20-hydroxy-13-methyl dammar-24-en-3-yl O-6-deoxy-α-L-mannopyranosyl-(1→2)-O-[β-D-glucopyranosyl-(1→3)]-β-D-glucopyranoside and Lotoside II is [(3β,15α,16β,22R)-16,22-epoxy-15,16,20-trihydroxydammar-24-en-3-yl O-6-deoxy-α-L-mannopyran-osyl-(1→2)-O-[β-D-glucopyranosyl-(1→3)]-β-D-glucopyranoside].

compound 17 is [(3β,24R,25R)-17,24-dihydroxyspirost-5-en-3-yl O-6-deoxy-α-L-mannopyranosyl-(1→2)-O-[β-D-glucopyranosyl-(1→3)]-β-D-glucopyranoside], compound 21 is [(3β)-21-(β-D-glucopyranosyloxy)-20-hydroxydammar-24-en-3-yl O-6-deoxy-α-L-mannopyranosyl-(1→2)-O-[β-D-glucopyranosyl-(1→3)]-β-D-glucopyranoside] and compound 25 is [(3β,16β,22R)-16,22:16,30-diepoxy-20-hydroxydammar-24-en-3-yl O-6-deoxy-α-L-mannopyranosyl-(1→2)-O-[β-D-glucopyranosyl-(1→3)]-β-D-glucopyranoside]

Where any preferred substituent (such as $C_{1-6}$ alkyl, $C_{1-6}$ hydroxyalkyl) is said to be composed of from 1 to 6 carbon atoms (ie $C_{1-6}$) such substituents are more preferred with 1 to 4 carbon atoms (ie $C_{1-4}$), are more preferred still with 1 or 2 carbon atoms (ie methyl or ethyl) and are most preferred with only one carbon atom (ie are in the methyl form). Likewise where partial substituents such as the $C_{1-6}$ alkyl group or $C_{1-6}$ alkoxy group of $C_{1-6}$-alkoxy-$C_{1-6}$-alkyl are said to be composed of from 1 to 6 carbon atoms (ie $C_{1-6}$) such substituents are, independently one of the other, more preferred with 1 to 4 carbon atoms (ie $C_{1-4}$), are more preferred still with 1 or 2 carbon atoms (ie methyl or ethyl) and are most preferred with only one carbon atom (ie are in the methyl form).

Alkyl, alkenyl and alykynyl radicals may, where the number of carbons in the chain permits, be either straight-chain or branched chain. $C_{1-6}$ alkyl radicals may be, for example, methyl, ethyl, n-propyl or iso-propyl, n-butyl, iso-butyl or tertiary-butyl, iso-pentyl, 2,2-dimethyl propyl, n-hexyl, iso-hexyl and 1,3-dimethylbutyl. $C_{1-6}$ alkenyl radicals may be, for example, allyl, 1-methylprop-2-enyl, 2-methylprop-2-enyl, 2-methyl prop-1-enyl, but-2-enyl, but-3-enyl, 1-methylbut-3-enyl, 1-methylbut-2-enyl, 3-methylbut-2-enyl; $C_{1-8}$ alkenyl radicals may be any of the $C_{1-6}$ alkyl radicals and may also be for example 5-methyl-hex-5-enyl, 4-methyl-hex-5-enyl, 3,4-dimethyl-hex-2-enyl $C_{1-6}$. Alkynyl may be, for example, propargyl, but-2-ynyl, but-3-ynyl, 1-methylbut-3-ynyl.

A $C_{1-6}$ hydroxyalkyl group may, where chemically possible, be either a $C_{1-6}$ monohydroxyalkyl or a $C_{1-6}$ dihydroxyalkyl group.

Where moieties may be, in turn, substituted by a saccharide moiety it is preferred that the bond is through an oxygen of the saccharide to form a group such as:

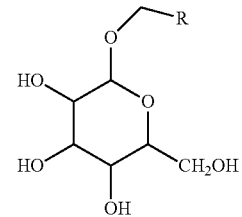

In the formula I the saccharide moieties comprise multiple chiral centres. Thus each of the carbon atoms 1, 2, 3, 4 and 5 of each saccharide can, independently, be in the R or S form. Depending on the form of the anomeric carbon, each saccharide can, independently, be in either the alpha or beta anomeric form. For Ring A the beta form is preferred. Depending on the arrangement around these chiral centres and the identity of the substituents $R^1$ and $R^2$ the individual monosaccharides can take a number of different forms. Thus for example, when $R^1$ is H and $R^2$ is —OH, the saccharide moiety may, for example, be arranged as arabinopyranose, lyxopyranose, ribopyranose or xylopyranose; preferably the saccharide is xylopyranose or arabinopyranose; more preferably the saccharide is xylopyranose.

When $R^1$ is —$CH_3$ and $R^2$ is —OH the saccharide moiety A is a 6-deoxy hexopyranose, and may be arranged as 6-deoxyallose, 6-deoxyaltrose, 6-deoxygalactose (fucose), 6-deoxyglucose (quinovose), 6-deoxygulose, 6-deoxyidose, 6-deoxymannose (rhamnose) or 6-deoxytalose preferably it is fucose or quinovose; most preferably it is quinovose.

Where $R^1$ is —CH$_2$OH and $R^2$ is —OH the saccharide moiety A is a hexopyranose and may be, for example, allose, altrose, galactose, glucose gulose, idose, mannose or talose; preferably it is galactose or glucose, and more preferably glucose.

Saccharides include, but are not limited to, monosaccharides, disaccharides, trisaccharides, tetrasaccharides and polysaccharides. Preferably saccharide moieties are monosaccharides, but may be independently selected as di- or oligosaccharides.

Monosaccharides include, but are not limited to, tetroses pentoses, hexoses and heptoses; tetroses pentoses and hexoses are preferred.

Tetroses may be for example aldotetroses, such as erithrose and threose and aldoketoses erithrulose.

Pentoses include, but are not limited to aldopentoses, such as arabinose, lyxose, ribose and xylose and ketopentoses such as ribulose and xylulose and deoxypentoses such as 2-deoxyribose and 3-deoxyribose. Preferred pentoses are xylose and arabinose. Pentoses may be in the furanose (eg arabinofuranose, lyxofuranose, ribofuranose and xylofuranose) or the pyranose (eg arabinopyranose, lyxopyranose, ribopyranose and xylopyranose) forms.

Hexoses include, but are not limited to aldohexoses, such as, allose, altrose, galactose, talose, gulose, idose, mannose and glucose (preferred are glucose, mannose, gulose, altrose, allose idose and talose) and ketokexoses such as fructose, psicose, sorbose and tagatose.

Hexoses may also he deoxy hexoses wherein an —OH group becomes an —H group at any position other than the bonded group. 6-deoxyhexoses are for example 6-deoxyallose, 6-deoxyaltrose, 6-deoxygalactose (fucose), 6-deoxyglucose (quinovose), 6-deoxygulose, 6-deoxyidose, 6-deoxymannose (rhamnose) or 6-deoxytalose. Deoxyhexoses may also be 2-deoxy, 3-deoxy, 4-deoxy and 5-deoxy hexoses. The oxygen may be lacking at more than one position. Examples of deoxyhexoses are—2-deoxy-glucose, 2-deoxygalactose, 4-deoxyfucose, 3-deoxygalactose, 2-deoxyglucose, 3-deoxyglucose, 4-deoxyglucose. Deoxyaldohexoses are preferred.

Hexoses also include hexosamines such as galactosamine, glucosamine and mannosamine, n-acteyl hexosamines such as N-acetyl-galactosamine, N-acetyl-mannosamine and N-acetylglucosamine. Preferred hexoses are aldohexoses and deoxy hexoses, particularly preferred hexoses are glucose, galactose, quinovose, fucose and rhamnose.

Hexoses may be in the furanose or pyranose form; preferably in the pyranose form.

Other monosaccharides include uronic acids, for example fructuronic acid, galacturonic acid, iduronic acid, glucuronic acid, guluronic acid, mannuronic acid and tagaturonic acid; sedoheptulose, sialic acid, neuraminic acid, muramic acid, N-acetylneuraminic acid, N-acetylmuramic acid, O-acetylneuraminic acid, and N-glycolylneuraminic acid.

Of hexoses, aldohexoses and deoxyhexoses (particularly deoxyaldohexoses) are preferred; of pentoses, aldopentoses and deoxy-pentoses (particularly deoxyaldopentoses) are preferred.

Pharmaceutically acceptable esters of compounds of the formula I are for example, an ester with an aliphatic or aromatic carboxylic or sulphonic acid. Aliphatic carboxylic acids may be for example of up to 6 carbon atoms, for example a methyl, ethyl, tent-butyl succinyl or malyl. Aromatic carboxylic acids may for example benzoic acid, sulphonic acids may be methylsulphonic or p-toluenesulphonic acid, and include esters at any available esterifiable position.

Pharmaceutically acceptable esters further include known compounds in which the sugar —OH groups are esterified with an aliphatic carboxylic acid of up to 6 carbon atoms. Also included are known esters at the carbon 26-position with compounds such as hydroxymethylgluteryric acid or its methyl ester (for example compound 19 and structure VI xxiv).

Pharmaceutically acceptable ethers are, for example, with $C_{1-6}$ hydroxyalkyl compounds which may be formed at any of the available —OH groups, for example on the saccharide moieties, or steroid moieties by converting one or more of the —OH groups to alkoxy groups (e.g. 61, 84, 85 incorporated herein by reference). A suitable pharmaceutically-acceptable salt form of the compounds of the formula I is, for example, an acid addition salt with an inorganic or organic acid, for example hydrochloric, hydrobromic, trifluoroacetic or maleic acid; or an alkali metal, for example sodium, an alkaline earth metal, for example calcium, or ammonium, for example tetra (2-hydroxyethyl)ammonium, salt.

Compounds of the formula I can be extracted from a variety of plant species. Examples of sources of compounds of the invention and example purification protocols are given in the references of table 2 (which are incorporated herein by reference). Further sources of compounds of the invention and methods of isolation of such compounds are detailed in (19—particularly in tables 2.2, 2.9, 2.10 and 2.11 and appendix 3 which are incorporated herein by reference) and references therein.

Many compounds of the invention are hydroxylated steroids. It is known in the art that such compounds, when exposed to solvent such as alcohols during purification or preparation, may be converted to alkoxy derivatives or to other derivatives such as methylketals (which revert to the original compounds upon drying). Particularly compounds of the formula IV, in which the carbon at the at the 22-position of the furostanol structure, is substituted by —OH, may be converted to alkoxy derivatives when exposed to alcohols. Notably such compounds may become methoxy derivatives when purified from plant sources using methanol-containing solvents. Alternatively they may be converted to the corresponding alkoxy by reflux in an appropriate anhydrous alcohol at elevated temperature, for example methanol (46). Such alkoxylated compounds are also compounds of the invention.

Where the compounds of the invention are purified from natural sources it is preferred that they are used in isolated form. By isolated is meant that the compound is at least 1% pure, conveniently it is at least 10% pure, more conveniently at least 30% pure, preferably it is at least 50% pure more preferably it is at least 80% pure still more preferably it is at least 90% pure and most preferably it is at least 95% pure.

The purity of the compound is conveniently expressed as a ratio of UV absorption associated with the compound to UV absorption associated with other material in the sample, conveniently at 205 nm. The purity of the compound may be measured for example using a chromatography system such as for example TLC or HPLC such as are described in the references herein, particularly in those references relating to the compound in question, or in applicants co pending application PCT/GB2004/005398.

Alternatively, compounds of the invention can be synthesised via a number of routes known to the skilled worker. For example by glycosylation of appropriate aglycones.

A number of suitable aglycones are available commercially, alternatively an suitable aglycone may be prepared, either by isolation from a natural source (see 19 and references therein), by deglycosylation of a suitable glycosylated compound (for example those compounds disclosed in (19) or herein), or by chemical synthesis from a variety of starting material that are readily available.

The skilled worker will be aware of many sources of spirostanol and furostanol aglycones suitable for preparing compounds for use in the invention. For example spirostanol aglycones wherein X=O or X=NH may be, for example, sarsapogenin, smilagenin, 12β-hydroxysmilagenin, Rhodeasapogenin, Isorhodiasapogenin, Samogenin, 12β-hydroxysamogenin, Markogenin, Yonogenin, Convallagenin A, Convallagenin B, Tokorogenin, Tigogenin, Neotigogenin, Gitogenin, Agigenin Digitogenin, Chlorogenin, Paniculogenin, (25R)-Spirostan-3β, 17α21-triol, Allogenin, (25R)-5α-Spirostan-2α,3β,5α,6α-tetraol, (24S, 25R)-5α-Spirostan-2α,3β,5α,6β,24-pentaol, Yamogenin Diosgenin, Yuccagenin, Lilagenin, Ruscogenin, (25S)-Ruscogenin, Neopraserigenin, Pennogenin, Isonuatigenin, Cepagenin, 24a-hydroxypennogenin, Ophiogenin, Sibiricogenin, Convallamarogenin, Neoruscogenin, Hecogenin, Neohecogenin, Manogenin, Sisalagenin, Solasodine, Soladulcidine, Tomatidine and 5-dehydrotomatidine.

Deglycosylation of, for example steroidal glycosides, may be simply carried out by acid hydrolysis, for example in a 50:50 mix of 2N HCl:dioxane at 100° C. in a sealed tube for 4.5 hrs (46).

Methods for the synthesis of a number of steroidal aglycones have been known for may years. For example synthesis of diosgenin, yamogenin, kryptogenin and isonarthogenin have been reported by the group of Kessar et al (61, 62, 63).

General synthetic routes to a variety of tri saccharide substituted spirostanol saponins are known (21, 22, 24, 25). Methods of synthesis of spirostanol saponins having 2,3 branched oligosaccharide moieties are also known (20, 29, 32). Methods of synthesis of furostanol saponins, synthesis of derivatised saponins and interconversion of spirostanol and furostanol saponins have also been devised (23, 25-27, 30, 31, 33, 34). Furthermore, furostanol and spirostanol saponins can be inter converted using a β-glucosidase (36) and pseudosaponins maybe cyclised to form the spirostanol derivative (34).

Combinatorial approaches to saponin synthesis have also been reported (35, 23).

These references also provide information and further references on derivatisation of saccharide hydroxyalkyl groups and are incorporated herein by reference.

As used herein the term aglycone refers to steroidal glycosides wherein the saccharide moieties are not present. The compounds may have other substituents at the position occupied by the saccharide moiety. Particularly aglycones that are furostanol saponins when glycosylated may be in the ring closed state as the equivalent spirostanol compounds. Steroidal glycosides are compounds having a steroid or substituted steroid core, to which is attached one or more saccharide moieties. A steroidal sapogenin is the aglycone of a steroidal saponin. A steroidal saponin is a naturally occurring steroidal glycoside.

An anti cell adhesion agent is an agent that reduces the adhesion of cells to a substrate such as platelets or the lining of blood vessels or other tissues, an anti cell-cell interaction agent is an agent that reduces the interaction between cells. An anti cellular extravasation agent is an agent that reduces the passage of cells from the blood stream through the walls of blood vessels.

For the avoidance of doubt the term $C_{1-6}$ acyl is —CO—$C_{1-5}$-alkyl.

The term "treating", as used herein, includes treating as prophylaxis or treatment of a current or remitting illness.

In a second aspect of the invention is provided the use of the compounds of the formula I in the manufacture of a medicament for the treatment of conditions involving detrimental activity of the enzyme core 2 GlcNAc-T, particularly raised activity. Examples of such conditions are described herein in the first aspect of the invention.

In a third aspect of the invention there are provided pharmaceutical compositions for use in treating conditions involving detrimental activity of the enzyme core 2 GlcNAc-T, particularly raised activity, comprising the compounds of the formula I. These compositions preferably further comprise pharmaceutically acceptable carriers, diluents or excipients.

In a fourth aspect of the invention is provided the use of compounds of the invention as anti cell adhesion agents, anti extravasation agents and anti cell-cell interaction agents.

Medicaments of the invention comprising compounds of the formula I will typically be prepared in a sterile and pyrogen free form. They can be administered by oral or parenteral routes, including intravenous, intramuscular, intraperitoneal, subcutaneous, transdermal, airway (aerosol), rectal, vaginal and topical (including buccal and sublingual) administration.

The medicament may be made up in liquid form in which case it will typically, in addition to the compound of the formula I, comprise a pharmaceutically acceptable diluent or it may be made up in solid form.

For oral administration, the compounds of the invention will generally be provided in the form of tablets or capsules, as a powder or granules, or as an aqueous solution or suspension.

Tablets for oral use may include the active ingredients mixed with pharmaceutically acceptable excipients such as inert diluents, disintegrating agents, binding agents, lubricating agents, sweetening agents, flavouring agents, colouring agents and preservatives. Examples of suitable inert diluents include sodium and calcium carbonate, sodium and calcium phosphate, and lactose, while corn starch and alginic acid are examples of suitable disintegrating agents. Binding agents include, for example starch and gelatine, while the lubricating agent, if present, may for example, be magnesium stearate, stearic acid or talc. If desired, the tablets may be coated with an enteric coating material, such as glyceryl mono stearate or glyceryl distearate, to delay absorption in the gastrointestinal tract. Capsules for oral use include hard gelatine capsules in which the active ingredient is mixed with a solid diluent, and soft gelatine capsules wherein the active ingredients is mixed with water or an oil such as peanut oil, liquid paraffin or olive oil Formulations for rectal administration may for example be presented as a suppository with a suitable base comprising, for example, cocoa butter or a salicylate.

Formulations suitable for vaginal administration may for example be presented as pessaries, tampons, creams, gels, pastes, foams or spray formulations containing in addition to the active ingredient such carriers as are known in the art to be appropriate.

In preparations for intramuscular, intraperitoneal, subcutaneous and intravenous use, the compounds of the invention will typically be provided in a pharmaceutically acceptable diluent to provide sterile solutions, emulsions, liposome formulations or suspensions. Typically the preparation will be buffered to an appropriate pH and isotonicity. For example suitable diluents include Ringer's solution and isotonic sodium chloride. Aqueous suspensions according to the invention may include suspending agents such as cellulose derivatives, sodium alginate, polyvinylpyrrolidone and gum tragacanth, and a wetting agent such as lecithin. Suitable preservatives include ethyl and n-propyl p-hydroxybenzoate.

The isolated Core 2 GlcNAc-T inhibitors of the invention may also be incorporated into a food or beverage product.

In general a suitable dose of Core 2 GlcNAc-T inhibitor will be in the range of 100 ng to 10 mg per kilogram body weight of the recipient per day, preferably in the range of 1 µg to 5.0 mg/kg/d. Typically the desired dose is presented once daily or several s a day in sub doses. These sub-doses may be administered in unit dosage forms, for example, containing 1 µg to 1500 mg, preferably 40 µg to 1000 mg, and most preferably 50 µg to 700 mg of active ingredient per unit dosage form.

The present invention will now be described further by reference to the following non-limiting Examples, Schemes and Figures. Further embodiments falling within the scope of the claim will occur to those skilled in the art in the light of these

FIGURES

FIG. 1: is a schematic diagram illustrating the process of purifying protogracillin and gracillin for *Dioscorea radix* tissue. Purification of dioscin is included for reference. Also illustrated are the purification of protodioscin and pseudoprotodioscin, which may also be purified from *Dioscorea radix*.

FIG. 2: illustrates the structures of protogracillin and gracillin isolated from *D. radix*.

EXAMPLES

TABLE 1

Example compounds of the invention

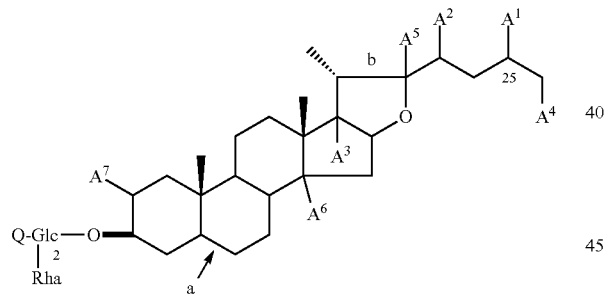

Table 1a

| Comp. | Q | $A^1$ | $A^2$ | $A^3$ | $A^4$ | $A^5$ | $A^6$ | $A^7$ | 25 R/S | Bond a | Bond b |
|---|---|---|---|---|---|---|---|---|---|---|---|
| 1 | 3-Glc | Me | H | H | Glc | OH | H | H | R | Double | Single |
| 2 | 3-Glc | Me | H | H | Glc | OH | H | H | S | Double | Single |
| 3 | 3-Glc | Me | H | H | Glc | OMe | H | H | R | Double | Single |
| 4 | 3-Glc | Me | H | H | Glc | OMe | H | H | S | Double | Single |
| 5 | 3-Glc | Me | H | H | Glc | Absent | H | H | R | Double | Double |
| 6 | 3-Glc | Me | H | H | Glc | Absent | OH | H | R/S | Double | Double |
| 7 | 3-Glc | Me | OMe | H | Glc | Absent | OH | H | R | Double | Double |
| 8 | 3-Glc | Me | H | H | Glc | OH | OH | H | R/S | Double | Single |
| 9 | 3-Glc | Me | H | H | Glc | H | H | OH | S | Single | Double |

TABLE 1-continued

Example compounds of the invention

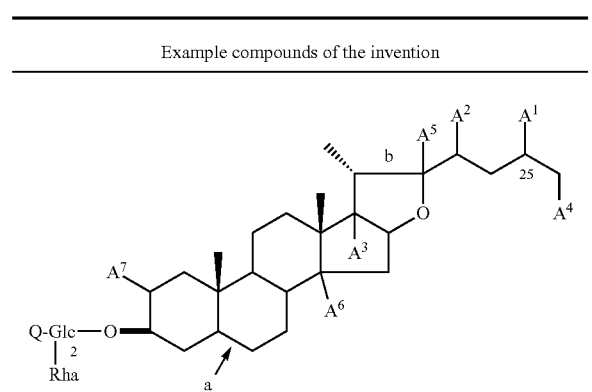

Table 1a

| Comp. | Q | $A^1$ | $A^2$ | $A^3$ | $A^4$ | $A^5$ | $A^6$ | $A^7$ | 25 R/S | Bond a | Bond b |
|---|---|---|---|---|---|---|---|---|---|---|---|
| 10 | 3-Glc | Me | H | H | OH | OMe | F | H | R | Double | Single |
| 27 | 4-Glc | Me | H | H | Glc | OH | H | H | S | Double | Single |
| 28 | 4-Glc | Me | H | H | Glc | OH | H | H | S | Single | Single |

TABLE 1b

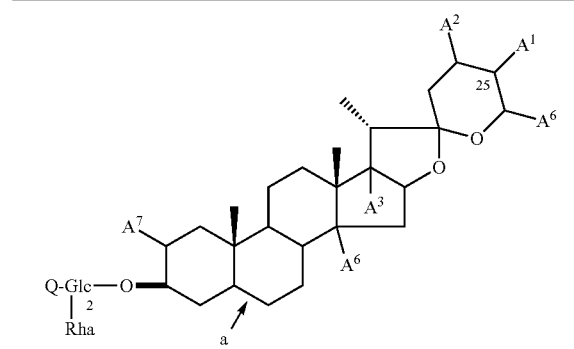

| Comp. | A | $R_1$ | $R_2$ | $R_3$ | $R_4$ | $R_5$ | $R_6$ | 25R/S | Bond a |
|---|---|---|---|---|---|---|---|---|---|
| 11 | 3-Glc | Me | H | H | H | H | H | R | Double |
| 12 | 3-Glc | Me | H | H | H | H | H | S | Double |
| 13 | 3-Glc | Me | H | OH | H | H | H | R | Double |
| 14 | 3-Glc | Me | H | H | OH | H | H | R/S | Double |
| 15 | 3-Glc | Me | OH | H | OH | H | H | S | Double |
| 16 | 3-Glc | =CH$_2$ | H | H | H | H | H | — | Double |
| 17 | 3-Glc | Me | OH | OH | H | H | H | R | Double |
| 18 | 3-Glc | —CH$_2$OH | H | H | H | H | H | R | Double |
| 19 | 3-Glc | * | H | H | H | H | H | R | Double |
| 29 | 4-Glc | Me | H | H | H | H | H | S | Single |

Substituent "*" = 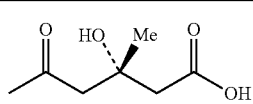

Compounds 27, 28 and 29 illustrate the structures of reference compounds in table 2

TABLE 1c

| Compound | Structure |
|---|---|
| 20 | 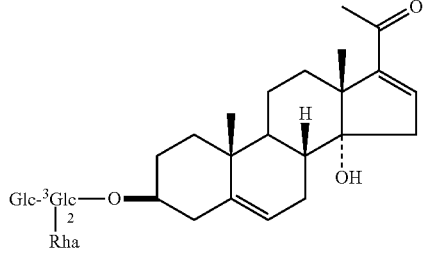 |
| 21 | 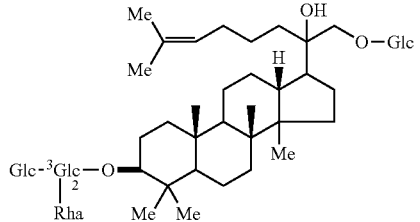 |
| 22 | 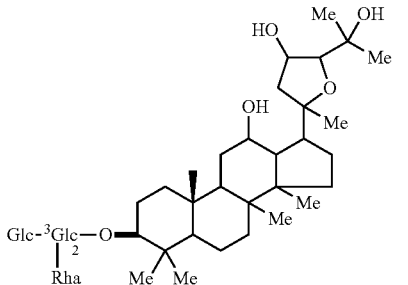 |
| 23 | 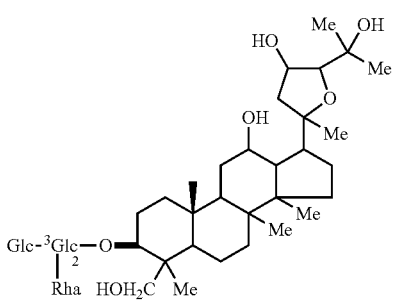 |
| 24 | 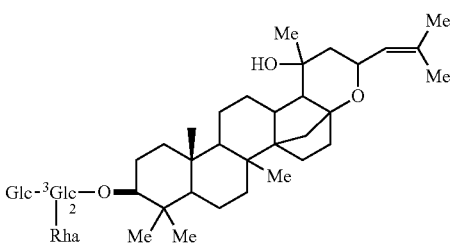 |

TABLE 1c-continued

| Compound | Structure |
|---|---|
| 25 | 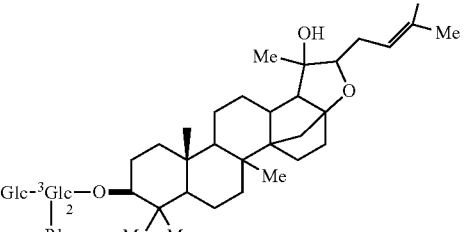 |
| 26 | 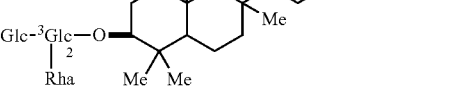 |

TABLE 2

Key to compound names and example references.

| Compound | Example references | Compound name |
|---|---|---|
| 1 | 46 | Protogracillin |
| 2 | 46, 57 | protoneogracillin |
| 3 | 44, 46, 58, 60 | Methylprotogracillin |
| 4 | 46 | Methprotoneogracillin |
| 5 | 88 | Pseudoprotogracillin |
| 6 | 43 | Dracenoside Q |
| 7 | 43 | Dioscoreside E |
| 8 | 43 | Dracenoside P |
| 9 | 40 | Tuberoside C |
| 10 | 39 | Icogenin |
| 11 | 28, 41, 45, 48, 57 | Gracillin |
| 12 | 47, 66 | Collettiside IV ((25S) Gracillin |
| 13 | 48, 65 | 17-OH Gracillin |
| 14 | 43 | Dracaenoside H |
| 15 | 43 | Dracaenoside L |
| 16 | 43 | Dracaenoside I |
| 17 | 48, 65 | Not named |
| 18 | 49 | Lilioglycoside H |
| 19 | 49 | Lilioglycoside I |
| 20 | 43 | Dracaenoside D |
| 21 | 50 | Not named |
| 22 | 51 | Neoalsoside A |
| 23 | 51 | Neoalsoside C |
| 24 | 52 | Hoduloside V |
| 25 | 53 | Not named |
| 26 | 54 | Lotoside II |
| 27 | 18 | Trigoneoside IVa ** |
| 28 | 64 | Shatavarin I ** |
| 29 | 64 | Shatavarin IV ** |

** = reference compounds

Example 1

Preparation of Compounds of the Invention: Preparation and Purification of *Dioscorea radix* Extracts Extraction: Dried, powdered *Dioscorea radix* (6.2 Kg) was extracted three times with MeOH—H$_2$O (8:2, 36 L, 26 L and 24 L, respectively). The first extract (CDXA-13-148-1) was concentrated to 5 L by evaporation under vacuum. The second and third extracts (CDXA-13-148-2 and 13-148-3) were combined and concentrated to 3,3 L.

Fractionation: The concentrated extracts were loaded on to a Dianion HP20 column (2.7 Kg) in 2.0 L batches and eluted with $H_2O$ and $H_2O$-MeOH (8:2, 6:4 and 4:6 and MeOH 1 L each). The column eluent was monitored by TLC and 8 fractions were collected (CDXA-13-149-1 to 8).

Column Chromatography 1: CDXA-13-149-4 and 13-149-5 were combined (45.4 g), absorbed on to silica gel (101 g), loaded on to a silica gel column (255 g) and eluted with EtOAc-MeOH—$H_2O$ (80:20:3, 1.7 L; 75:25:3, 2.0 L; 70:30:4, 1.04 L; 65:35:4, 2.08 L; and 60:40:5, 1,05 L). The eluent was monitored by TLC and 26 fractions were collected (CDXA-13-166-F1 to F26).

Column Chromatography 2: CDXA-13-166-F14 to F22 were combined (25.2 g), absorbed on to silica gel (48.2 g), loaded on to a silica gel column (305 g), and eluted with EtOAc-MeOH—$H_2O$ (80:20:3, 600 ml; 75:25:3, 4120 ml; 70:30:4, 2080 ml; 65:35:4, 1050 ml; and 60:40:5, 1050 ml). The eluent was monitored by TLC and 28 fractions were collected (CDXA-13-167-F1~F28).

Purification of Protogracillin: Fractions 13-167-F5 to F16 were combined and concentrated under vacuum, the white powder separated was filtered, dried (CDXA-13-167-K5, 2.27 g) and heated under refluxed in ACN—$H_2O$ (28:72; 100 ml) at 90° C. oil bath overnight. The product was further purified by HPLC (Novaprep 5000 semi-preparative HPLC column (C18, 5.0×20.0 cm) eluted with ACN—$H_2O$ (25:75) for 41.2 minutes then eluted with ACN—$H_2O$ (50:50) for another 20 minutes at a flow rate of 100 ml/minute. Monitored at UV 205 nm and the major peak was collected) to give two batches of protogracillin (CDXA-13-168-1, 374 mg; CDXA-13-169-1, 552 mg).

Purification of dioscin and gracillin: Fraction CDXA-13-149-F6 (22.4 g) was loaded on to a C18 column (296 g, 5×20 cm), eluted with MeOH-H2O (3:7, 4:6, 45:55, 50:50, 55:45, 60:40, 65:35,7:3, 75:25, 80:20, 85:15 and 90:10, 1000 ml each), and 8 fractions were collected (CDXA-13-159-F1 to F8). Fraction CDXA-13-159-F7 (4.5 g) was separated on silica gel (257 g silica gel) eluting with EtOAc-MeOH—H2O (85:15:2, 1020 ml; 80:20:3, 3090 ml; 75:25:3, 1030 ml) giving 14 fractions (CDXA-13-160-F1 to F14). The fractions CDXA-13-160-F2 and F3 gave dioscin (CDXA-13-160-1, 404 mg) while fraction CDXA-13-160-F4 gave gracillin (CDXA-13-160-2, 195 mg) both as white powders.

Protogracillin was 96.7% pure as a white powder
Gracillin was 90.8% pure as a white powder

TABLE 3

$^{13}$C NMR data of the compounds from Dioscorea (in pyridine-d5)

| | Gracillin 13-160-2 | Dioscin 13-160-1 | Protogracillin 13-168-1 |
|---|---|---|---|
| 1 | 37.8 | 37.8 | 37.8 |
| 2 | 30.4 | 30.5 | 30.4 |
| 3 | 78.3 | 78.4 | 78.9 |
| 4 | 39.0 | 39.3 | 39.0 |
| 5 | 141.1 | 141.1 | 141.1 |
| 6 | 122.1 | 122.2 | 122.3 |
| 7 | 32.7 | 32.6 | 32.7 |
| 8 | 32.1 | 32.0 | 32.0 |
| 9 | 50.6 | 50.6 | 50.6 |
| 10 | 37.5 | 37.5 | 37.5 |
| 11 | 21.4 | 21.4 | 21.4 |
| 12 | 40.2 | 40.2 | 40. |
| 13 | 40.8 | 40.8 | 41.1 |
| 14 | 57.0 | 56.9 | 56.9 |
| 15 | 32.6 | 32.5 | 32.8 |
| 16 | 81.4 | 81.4 | 81.5 |
| 17 | 63.2 | 63.2 | 64.2 |
| 18 | 16.7 | 16.7 | 16.8 |
| 19 | 19.7 | 19.7 | 19.7 |
| 20 | 42.3 | 42.3 | 41.0 |
| 21 | 15.4 | 15.4 | 16.8 |
| 22 | 109.6 | 109.6 | 111.0 |
| 23 | 32.0 | 32.1 | 37.6 |
| 24 | 29.6 | 29.6 | 28.7 |
| 25 | 30.9 | 30.9 | 34.6 |
| 26 | 67.2 | 67.2 | 75.6 |
| 27 | 17.7 | 17.7 | 17.8 |
| 3-O— | | | |
| Glc1 | 100.3 | 100.6 | 100.3 |
| 2 | 78.0 | 78.4 | 78.0 |
| 3 | 89.9 | 78.1 | 89.9 |
| 4 | 69.9 | 78.8 | 69.9 |
| 5 | 77.3 | 77.3 | 77.3 |
| 6 | 62.7 | 61.6 | 62.7 |
| Rha1' | 102.6 | 102.4 | 102.6 |
| 2' | 72.8 | 72.9 | 72.8 |
| 3' | 73.1 | 73.2 | 73.1 |
| 4' | 74.4 | 74.5 | 74.5 |
| 5' | 69.9 | 69.9 | 69.9 |
| 6' | | 18.9 | 19.1 |
| Glc1/rha 1" | 104.9 | 103.2 | 104.9 |
| 2" | 75.3 | 72.9 | 75.3 |
| 3" | 79.0 | 73.1 | 78.9 |
| 4" | 71.8 | 74.2 | 71.8 |
| 5" | 78.9 | 70.7 | 78.9 |
| 6" | 62.7 | 19.0 | 62.8 |
| 26-O— | | | |
| Glc1''' | | | 105.3 |
| 2''' | | | 75.6 |
| 3''' | | | 79.1 |
| 4''' | | | 72.0 |
| 5''' | | | 79.0 |
| 6''' | | | 63.1 |

Mass Spec and $^1$H NMR Data of the Compounds Isolated from Dioscorea:

Gracillin: (+) ESI-MS m/z 907.56 [M+Na$^+$]; $^1$H NMR. (400 Hz, $C_5D_5N$) δ 0.69 (3H, d, J5.6 Hz, 27-$H_3$), 0.83 (3H, s, 18-$H_3$), 1.07 (3H, s, 19-$H_3$), 1.14 (3H, d, J=7.2 Hz, 21-$H_3$), 1.79 (3H, d, J=6.4 Hz, rha 6'-$H_3$), 4.96 (1H, d, J=7.2 Hz, glc 1-H), 5.12 (1H, d, J=7.6 Hz, glc 1"-H), 5.33 (1H, d, J=5.2 Hz, 6-H), 6.41 (1H, s, rha 1'-H).

Protogracillin: (+) ESI-MS m/z 1087.56 [M+Na$^+$]; $^1$H NMR (400 Hz, $C_5D_5N$) δ 0.91 (3H, s, 18-$H_3$), 1.00 (3H, d, J=6.4 Hz, 27-$H_3$), 1.08 (3H, s, 19-$H_3$), 1.35 (3H, d, J=6.8 Hz, 21-$H_3$), 1.78 (3H, s, J=6,0 Hz, Rha-6"-$H_3$), 4.84 (1H, d, J=7.6 Hz, Glc-1"-H), 4.97 (1H, d, J=6.8 Hz, Glc-1'-H), 5.13 (1H, d, J=8.0 Hz, glc 1"-H), 5.33(1H, d, J=4.0 Hz, 6-H), 6.42 (1H, s, Rha-1'-H).

Dioscin: (+) ESI-MS m/z 891.55 [M+Na$^+$]; $^1$H NMR (400 Hz, $C_5D_5N$) δ 0.70 (3H, d, J=4.8 Hz, 27-$H_3$), 0.84 (3H, s, 18-$H_3$), 1.06 (3H, s, 19-$H_3$), 1.15 (3H, d, J=6.8 Hz, 21-$H_3$), 1.66 (3H, d, J=4.8 Hz, rha 6"-$H_3$), 1.79 (3H, d, J=6.4 Hz, rha 6'-$H_3$), 4.97 (1H, d, J=6.8 Hz, glc 1-H), 5.31 (1H, d, J=4.0 Hz, 6-H), 5.91 (1H, s, rha 1"-H), 6.45 (1H, s, rha 1'-H).

Example 2

Biological Activity of Compounds.

2a. Cell Culture

The human leukocytic cell-line (U937) was cultured in RPMI supplemented with 10% foetal calf serum, 2 mM glutamine, 100 IU/ml penicillin and 100 µg/ml streptomycin, 2b. Assay of Core 2 GlcNAc-T Activity Three approaches may be used:

(i). Glucose induction of Core 2 GlcNAc-T leukocytes (U937 cells) are exposed to normal glucose (5.8 mM) or high glucose (15 mM) for 24 hours at 37° C. After incubation, the cells maybe lysed and frozen at −20° C. until used for the measurement of core 2 GlcNAc-T, or used immediately.

(ii). TNF-α induction of core 2 GlcNAc-T. Human leukocytes (U937 cells) are exposed to human recombinant TNF-alpha (8 pg/ml) in the presence and absence of test compounds After 24 h incubation, the activity of core 2 GlcNAc-T was measured, and expressed as pmoles/h/mg protein (iii). Cell free assay of core 2 GlcNAc-T in cell free assays of core 2 GlcNAc-T Heart lysates from either from TNF-alpha over expressing transgenic mice (female, B6.SJL-Tg (TNF) supplied by Taconic-M+B, Bomholtveg 10, 8680 Ry, Denmark) or from BB rats (89) was exposed to various concentrations of test compound for 1 h at 37° C. Activity of core 2 GlcNAc-T was measured, and expressed as pmoles/h/mg protein.

2c. Measurement of Core 2 GlcNAc-T Activity:

To measure core 2 GlcNAc-T activity, leukocytes were washed in PES, frozen and lysed in 0.9% Triton X-100 at 0° C., The activity of core 2 GlcNAc-T was measured as described previously (16). Cell free assays are preformed by substituting heart lysates for cell lysates.

Assays were performed in 50 mM 2(N-morpholino) ethanesulfonic acid (MES, Sigma, Dorset, UK), pH 7.0, 1 mM UDP-6 ['H]-N-acetylglucosamine (16,000 dpm/nmol, NEN Life Science Products, Hounslow, UK), 0,1 M GlcNAc (Sigma, Dorset, Okla.), 1 mM Galβ1-3GalNAcα-p-nitrophenol (Sigma, Dorset, UK) as substrate, and 16 µl of lysate (100-200 µg protein) for a final volume of 32 µl. After incubating the mixture for 1 hour at 37° C., the reaction was terminated with 1 ml of ice-cold distilled water and processed on a C18 Sep-Pak column (Waters-Millipore, Watford, UK). After washing the column with 20 ml of distilled water, the product was eluted with 5 ml of methanol. The radioactivity of the samples was counted in a liquid scintillation β-counter (LKB-Wallac, London, UK). Endogenous activity of core 2 GlcNAc-T was measured in the absence of the added acceptor. The specific activity was expressed as pmoles/h/mg of cell protein. In each case, the protein concentration was determined with BioRad protein assay (BioRad, Hertfordshire, UK).

TABLE 4

Approximate Ic$_{50}$ values (nM) for example compounds

| Compound | Number | Cell free assay * | Cell based assay |
|---|---|---|---|
| Protogracillin | 1 | 3 | 0.25 |
| Gracillin | 18 | 4.5 | 2.5 |
| Trigoneoside IVa*** | 43 | 0.9 | 0.75 |
| Shatavarin I*** | 44 | 1 | 0.75 |
| Shatavarin IV*** | 45 | ** | † |

* Assays carried out on heart lysates of TNF-α mice as described above.
** 89% inhibition of core 2 GlcNAc-T at 22 nM
*** reference compounds
† = no activity detected at 22.5 nM.

TABLE 5

Approximate purities of compounds used

| Compound | Number | Approximate purity by HPLC |
|---|---|---|
| Protogracillin | 1 | 96.7 |
| Gracillin | 18 | 98 |
| Trigoneoside IVa | 43 | 89% |
| Shatavarin I | 44 | >95% |

References

1. Ellies L. G. et al., *Immunity* 9, 881-890 (1998)
2. Brockhausen I. et al. *Cancer Res.* 51, 1257-1263 (1991)
3. Renkonen J. et al., *APMIS* 109, 500-506 (2001)
4. Machida E. et al. *Cancer Res.* 61, 2226-2231 (2001)
5. Dalziel M. et al. *Biol. Chem.* 276, 1 1007-1 1105 (2001)
6. Perandio M. et al. *Blood* 97, 3812-3819 (2001)
7. Yousefi S. et al *J. Biol. Chem.* 266, 1772-1782 (1991)
8. Higgins E. A. et al. *J. Biol. Chem.* 266, 6280-6290 (1991)
9. Piller F. et al. *J. Biol. Chem.* 263, 15146-15150 (1988)
10. Koya D. et al. *FASEB J.* 13, 2329-2337 (1999)
11. Nishio Y, et al. *J. Clin. Invest.* 96, 1759-1767 (1995)
12. Tsuboi S. et al *Bioassays* 23, 46-53 (2001)
13. Tsuboi S. et al. *EMBO J.* 16, 6364-6373 (1997)
14. Tsuboi S. et al. *Bioassays* 23, 46-53 (2001)
15. Tsuboi S. et al. *J. Biol. Chem.* 273(46), 30680-30687 (1998)
16. Chibber R. et al. *Diabetes* 49, 1724-1730 (2000)
17. Kuhns W. et al. *Glycoconjugate Journal* 10 381-394
18. Yoshikawa M. et al. *Heterocycles* 47, 397-405 (1998).
19. Hostettman K. Saponins. Cambridge University Press UK. (1995).
20. Li C et al. *Carbohydr Res.;* 306(1-2):189-95. (1998).
21. Deng S et al. *Carbohydr Res.;* 30; 317(1-4):53-62. (1999)
22. Li B et al. 9; 331(1):1-7. (2001).
23. Vu B et al. *J. Comb Chem,;* 3(5):404-6, (2001).
24 Yu B. et al. Tetrahedron letters, 42, 77-79 (2001).
25. Yu B et al. *J Org Chem.;* 13; 67(25):9099-102 (2002).
26. Cheng M. S. et al. *J Org Chem,;* 2; 68(9):3658-62 (2003)
27 Du Y et al. *Org Lett.;* 2; 5(20):3627-30,(2003).
28. Tsukamoto T and Kawasaki T. *Pharm Bull* 4(2):104-8 (1956).
29. Zou C. C. et al *Carbohydr Res.* 4; 338(8): 721-7 (2003).
30. Li M et al *Carbohydr Res.* 20; 338(2): 117-21 (2003).
31. Lahmann M et al *Carbohydr Res.* 337(21-23): 2153-9 (2002).
32. Gu G et al *J Org Chem,* 69(16):5497-500 (2004).
33. Wang S. M. et al *Steroids.* 69(10): 599-604 (2004).
34. Tobari A. et al *Eur J Med Chem.* 35(5): 511-27 (2000).
35. Lautrette S. et al *Chem Commun (Camb).* 7; (5): 586-7 (2004).
36. Inoue K. *Phytochemistry* 41(3), 725-7(1996).
37. Hindsgaul O. *J Biol Chem.* 266(27):17858-62 (1991).
38. Toki D, et al *Biochem Biophys Res Commun.* 198(2): 417-23 (1994).
39. Hernandez, J. C. *Bioorganic & Medicinal Chemistry* 12(16), 4423-4429 (2004).
40. Sang S. *Phytochemistry,* 52(8), 1611-1615 (1999).
41. Inoue T, et al *Phytochemistry* 40(2), 521-5 (1995).
42. Mimaki Y. et al *Natural Product Letters,* 14(5), 357-364 (2000).
43. Zheng Q. et al *Steroids,* 69(2), 111-119 (2004).
44. Yang D. et al *Journal of Agricultural and Food Chemistry,* 51(22), 6438-6444 (2003).

45. Kawasaki T. et al *Chemical & Pharmaceutical Bulletin*, 22(9), 2164-75 (1974).
46. Hu K. *Planta Medica*, 63(2), 161-165 (1997).
47. Tang S. et al *Yunnan Zhiwu Yanjiu*, 9(2), 233-8 (1987).
48. Chen C. et al *Yunnan Zhiwu Yanjiu*, 9(4), 495-502 (1987).
49. Kintya P. (Translation of *Khimiya Prirodnykh Soedinenii*), [Volume Date 1997], 33(6), 658-662 (1998).
50. Yin F. et al *J. Nat. Products*, 67(6), 942-952 (2004).
51. Fujita S. et al *Phytochemistry*, 38(2), 465-72 (1995).
52. Yoshikawa K et al. *Chemical & Pharmaceutical Bulletin*, 40(9), 2287-91 (1992).
53. Yoshikawa K. et al *Chemical & Pharmaceutical Bulletin*, 40(9), 2275-8 (1992).
54. Renault J. et al, *Phytochemistry*, 44(7), 1321-1327 (1997).
55. Dong M. et al *Planta Med*, 67(9):853-7 (2001).
56. Nakamura O. et al *Phytochemistry*, 36(2):463-7 (1994).
57. Mimaki Y, et al *Phytochemistry*. 33(3):675-82 (1993).
58. Aquino R. et al *J. Nat. Products* 49(2) 1096-1101 (1986).
59. Hu K. et al *Planta Med*. 62(6):573-5 (1996).
60. Tomova M. et al *Int Conf. Chem Biotechnol*. 3, (1)298-302.
61. Kessar S. et al *Tetrahedron*, 24(2):905-7 (1968).
62. Kessar S. et al *Tetrahedron* 24(2):899-904 (1968).
63. Kessar S. et al *Tetrahedron*. 24(2):887-92 (1968).
64. Ravikumar P. R. et al. *Indian J Chem*. 26B, 1012-1017 (1987).
65. Chen C. et al *Yunnan Zhiwu Yanjiu*, 6(1), 111-17 (1984).
66. Liu C. et al, *Yaoxue Xuebao*, 18(8), 597-606 (1983).
67. Kumar R et al *Blood*. 15; 88(10):3872-9 (1996).
68. Inoue T. et al *J Leukoc Biol*. 77(3):287-95 (2005).
69. Hansen A. et al *J Am Coll Cardiol*. 18; 44(4):887-91 (2004).
70. Tanguay J. et al *Thromb Haemost*. 91(6):1186-93 (2004).
71. Rijcken E, et al *Am J Physiol Gastrointest Liver Physiol*. 287(1):G115-24 (2004).
72. Dang B. et al *J Leukoc Biol*. 72(4):702-10 (2002).
73. Wang K. et al *Thromb Haemost*. 88(1):149-54 (2002).
74. Theoret J. et al *J Pharmacol Exp Ther*. 298(2):658-64 (2001).
75. Bienvenu J. et al *Circulation*. 27; 103(8);1128-34 (2001).
76. Stoica S. et al, *J Heart Lung Transplant*. 24(5):593-601 (2005).
77. Dedrick R. L. et al. *Expert Opin Biol Ther. February*; 3(1):85-95 (2003).
78. Matsuda H et al *Bioorg Med Chem Lett*. 24; 13(6): 1101-6 (2003).
79. Hu K and Yao X. *Anticancer Drugs*. 12(6):541-7 (2001).
80. Hu K and Yao X. *Phytother Res*. 17(6):620-6 (2003).
81. Kim S Y et al *Arch Pharm Res*. 22(3):313-6 (1999).
82. Oda K et al *Biol Chem*. 381(1):67-74 (2000).
83. Strauss E. et al *Invest Ophthalmol Vis Sci*. 40(7):1336-421 (1999).
84. Myers D. et al *Thromb Haemost*. 87(3):374-82 (2002).
85. Hickey M. et al, *J Immunol*. May 1; 168(9):4728-36 (2002).
86. Lanteri M. et al, *Glycobiology*. 13(12):909-18 (2003).
87. Yago T. et al *J Biol Chem*. 26; 278(39):37987-97 (2003).
88. Liu H. W. et al *J Asian Nat Prod Res*. 5(4):241-247 (2003).
89. Festing M. F. W. (Ed.). Inbred strains in biomedical research. The Macmillan Press LTD, London (1979). ISBN 0-333-23809-5.
90. Ori K. et al. *Phytochemistry*. 31(8):2767-75 (1992).
91. Shimomura H. et al., Phytochemistry 28, 3163-3170 (1989).

The invention claimed is:

1. A method of treating a subject in need of therapy for a condition involving detrimental activity of the enzyme core 2 GlcNAc-T comprising administering, to a patient having a condition involving detrimental activity of the enzyme core 2 GlcNAc-T selected from the group consisting of vascular diseases, autoimmune and inflammatory conditions, a therapeutically effective amount of an inhibitor of core 2 GlcNAc-T of formula I to a patient in need thereof

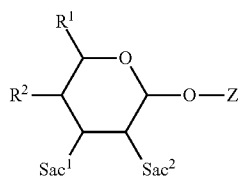

wherein:
R$^1$ is H, C$_{1-6}$ alkyl, C$_{1-6}$ hydroxyalkyl, C$_{1-6}$ alkoxy or C$_{1-6}$-alkoxy-C$_{1-6}$-alkyl;
R$^2$ is H, —OH or C$_{1-6}$ alkoxy;
Sac$^1$ and Sac$^2$ are independently selected saccharide moieties; and
Z is a steroid moiety;
or a pharmaceutically acceptable salt, ether or ester thereof.

2. A method according to claim 1 in which R$^1$ is —H, —CH$_3$ or —CH$_2$OH.

3. A method according to claim 1 in which R$^1$ is —CH$_2$OH.

4. A method according to claim 1 in which R$^1$ is —CH$_2$OH and a ring in the structure of formula I is a glucose moiety.

5. A method according to claim 1 in which R$^2$ is —OH.

6. A method according to claim 1 in which Sac$^1$ and Sac$^2$ are monosaccharides.

7. A method according to claim 1 in which Sac$^1$ is a pentose or an aldohexose.

8. A method according to claim 1 in which Sac$^1$ is an aldohexose.

9. A method according to claim 1 in which Sac$^1$ is glucose.

10. A method according to claim 1 in which Sac$^2$ is selected from the group consisting of a tetrose a pentose and a hexose moiety.

11. A method according to claims 1 in which Sac$^2$ is rhamnose.

12. A method according to claim 1 in which the compound of the formula I is

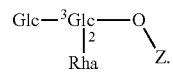

13. A method according to claims 1 in which the steroid moiety Z is a Compound of the formula:

VI

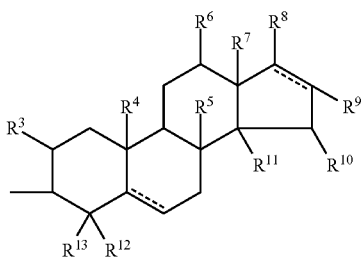

which steroid moiety Z may further incorporate a further group selected from the groups consisting of groups VI(a) to VI(e):

VIa

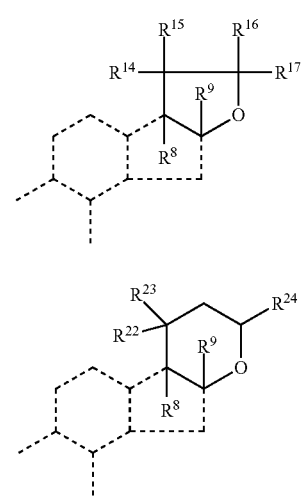

VIb

VIc

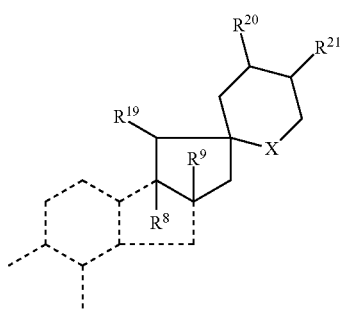

VId

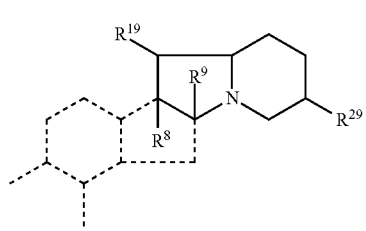

-continued

VIe

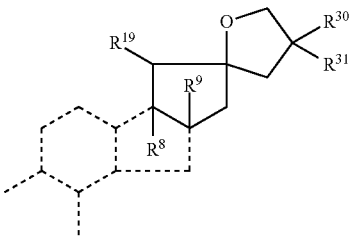

wherein:
$R^3$, $R^{10}$ and $R^{18}$ are independently selected from H and —OH;
$R^4$ and $R^{25}$ are independently selected from $C_{1-6}$ alkyl;
$R^5$, $R^7$ and $R^{12}$ are independently selected from H and $C_{1-6}$ alkyl;
$R^6$ is H or —OH or the H normally also present is absent and $R^6$ is =;
$R^8$ is H, —OH or $C_{1-6}$ acyl or a group selected from VII a or VII b.

VIIa

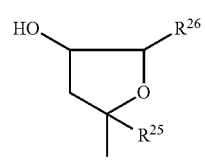

VIIb

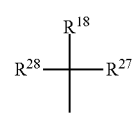

$R^9$ is H.
$R^{11}$ is H, $C_{1-6}$ alkyl or —OH or $R^9$ and $R^{11}$ taken together form a —CH$_2$—CH$_2$— group;
$R^{13}$ is H, $C_{1-6}$ alkyl or $C_{1-6}$ hydroxyalkyl;
$R^{14}$, $R^{19}$, $R^{23}$ and $R^{29}$ are independently selected from $C_{1-6}$ alkyl;
$R^{15}$ is H or —OH;
$R^{16}$ is H, —OH or $C_{1-6}$ alkoxy or $R^{15}$ and $R^{16}$ taken together represent the second bond of a double bond joining adjacent carbon atoms;
$R^{17}$ is $C_{1-6}$ alkyl, $C_{2-6}$ alkenyl, $C_{2-6}$ alkynyl or a $C_{1-6}$ alkyl group substituted by one or more groups selected from the group consisting of —OH, $C_{1-6}$alkoxy and Sac$^3$;
$R^{20}$ is H or —OH;
$R^{21}$ is $C_{1-6}$ alkyl, $C_{1-6}$ hydroxyalkyl or =CH$_2$;
$R^{22}$ is —OH; $R^{24}$ is $C_{1-6}$ alkyl, $C_{2-6}$ alkenyl or $C_{2-6}$ alkynyl;
$R^{26}$ is $C_{1-6}$ hydroxyalkyl;
$R^{27}$ is $C_{1-6}$ alkyl, $C_{1-6}$ hydroxyalkyl or $C_{1-6}$ alkyl substituted by Sac$^4$;
$R^{28}$ is $C_{1-8}$ alkyl, $C_{2-8}$ alkenyl or $C_{2-8}$ alkynyl;
$R^{30}$ is $C_{1-6}$ hydroxyalkyl or $C_{1-6}$ alkyl substituted by Sac$^5$;
$R^{31}$ is $C_{1-6}$ alkyl;
Sac$^3$ and Sac$^5$ are independently selected saccharide moieties;
Sac$^4$ is a saccharide;
X is either O or NH; and
--- Represents either a single bond or a double bond.
14. A method according to claims 13 in which $R^{17}$ is $C_{2-6}$ alkenyl or a $C_{1-6}$ alkyl group substituted by one or more groups selected from the group consisting of —OH, —OCH$_3$ and Sac$^3$.

15. A method according to claim 13 in which $R^{17}$ is selected from the group comprising 3-methyl but-2-enyl, 2-methyl-prop-2-enyl, 3-methylbutanyl substituted at the 4-position by $Sac^3$, 1-hydroxy-3-methylbutanyl substituted at the 4-position by $Sac^3$ or 1-methoxy-3-methylbutanyl substituted at the 4-position by $Sac^3$.

16. A method according to claim 13 in which $R^{21}$ is —$CH_3$, —$CH_2OH$ or =$CH_2$.

17. A method according to claim 13 in which $R^{24}$ is $C_{2-6}$ alkenyl.

18. A method according to claims 13 in which $R^{27}$ is —$CH_3$ or —$CH_2$-$Sac^4$.

19. A method according to claim 13 in which $Sac^4$ is glucose.

20. A method according to claim 13 in which $R^{28}$ is $C_{1-8}$ alkyl or $C_{2-8}$ alkenyl.

21. A method according to claim 13 in which $R^{28}$ is 3-ethyl-4-methyl-pentanyl or 5-methyl-hex-4-enyl.

22. A method according to claim 13 in which $R^{30}$ is —$CH_2$-$Sac^5$.

23. A method according to claim 13 in which $Sac^5$ is glucose.

24. A method according to claim 13 in which X is O.

25. A method according to claim 1 in which the compound is selected from the group consisting of:

Protogracillin protoneogracillin methylprotogracillin methylprotoneogracillin, pseudoprotogracillin, dracenoside Q, dioscoreside E dracenoside P tuberoside C, icogenin, gracillin, collettiside IV, 17-OH gracillin, dracaenoside H dracaenoside L, dracaenoside I, lilioglycoside H, lilioglycoside I, dracaenoside D, neoalsoside A, neoalsoside C, hoduloside V, Lotoside II, compound 17, compound 21 and compound 25.

* * * * *